US009822393B2

(12) United States Patent
Lowe et al.

(10) Patent No.: US 9,822,393 B2
(45) Date of Patent: Nov. 21, 2017

(54) COMPOSITIONS, METHODS AND SYSTEMS FOR POLYMERASE CHAIN REACTION ASSAYS

(71) Applicant: Bio-Rad Laboratories, Inc., Hercules, CA (US)

(72) Inventors: Adam Lowe, Mountain House, CA (US); Geoff McDermott, Pleasanton, CA (US); Christopher M. Hindson, Pleasanton, CA (US); Erin R. Chia, Berkeley, CA (US); Amy L. Hiddessen, Dublin, CA (US); Benjamin J. Hindson, Livermore, CA (US); Chunxiao Han, Dublin, CA (US); Yaqi Wang, Dublin, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 144 days.

(21) Appl. No.: 14/201,752

(22) Filed: Mar. 7, 2014

(65) Prior Publication Data

US 2014/0302503 A1 Oct. 9, 2014

Related U.S. Application Data

(60) Provisional application No. 61/775,415, filed on Mar. 8, 2013.

(51) Int. Cl.
*C12Q 1/68* (2006.01)
*B01L 7/00* (2006.01)
*B01L 3/00* (2006.01)

(52) U.S. Cl.
CPC .............. *C12Q 1/6804* (2013.01); *B01L 7/52* (2013.01); *C12Q 1/6844* (2013.01); *C12Q 1/6851* (2013.01); *B01L 3/502784* (2013.01)

(58) Field of Classification Search
CPC ................................................... C12Q 1/6804
USPC ......................................................... 435/6.1
See application file for complete search history.

(56) References Cited

U.S. PATENT DOCUMENTS

| | | |
|---|---|---|
| 2010/0022414 A1 | 1/2010 | Link et al. |
| 2010/0105112 A1 | 4/2010 | Holtze et al. |
| 2010/0173394 A1 | 7/2010 | Colston et al. |
| 2011/0250597 A1 | 10/2011 | Larson et al. |
| 2012/0208241 A1 | 8/2012 | Link |
| 2012/0219947 A1 | 8/2012 | Yurkovetsky et al. |

FOREIGN PATENT DOCUMENTS

| | | |
|---|---|---|
| CN | 101367932 A | 2/2009 |
| CN | 101 724 295 | * 6/2010 |

OTHER PUBLICATIONS

European Patent Application, "Extended European Search Report" in connection with related European Patent Application No. 14759550.8, dated Jul. 18, 2016, 8 pages.
Kintses, Balint et al., "Microfluidic droplets: new integrated workflows for biological experiments", www.sciencedirect.com, Current Opinion in Chemical Biology, vol. 14, Sep. 24, 2010, pp. 548-555.
Platzman, Ilia et al., "Synthesis of Nanostructured and Biofunctionalized Water-in-Oil Droplets as Tools for Homing T Cells", Journal of the American Chemical Society, vol. 135, Feb. 18, 2013, pp. 3339-3342.
Brouzes, et al. Droplet microfluidic technology for single-cell high-throughput screening. Proc Natl Acad Sci U S A. Aug. 25, 2009;106(34):14195-200.
Chen, et al. Chemical transfection of cells in picoliter aqueous droplets in floruocarbon oil. Anal. Che. 2011; 83:8816-8820.
Courrier, et al. Reverse water-in-fluorocarbon emulsions and microemulsions obtained with a fluorinated surfactant. Colloids and Surfaces: A Physicochem. Eng. Aspects. 2004; 244: 141-148.
Doan, et al. Dimerization of Carboxylic Acids and Salts: An IR Study in Perfluoropolyether Media. J. Am. Chem. Soc. 1997; 119:9810-9815.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
International search report and written opinion dated Jul. 28, 2014 for PCT/US2014/022163.
Kaltenbach, et al. A simple method to evaluate the biochemical compatibility of oil/surfactant mixtures for experiments in microdroplets. Lab Chip. Oct. 21, 2012;12(20):4185-92.
Kasai, et al. Grafting lubricant molecular chains to the carbon overcoat. Tribol Lett. 2008; 31:17-23.
Kasai. Perfluoropolyethers with acid end groups: Amphiphilicity and emulsification. Journal of Applied Polymer Science. 1995; 57:797-809.
Kasai. Perfluoropolyethers with acid end groups: An ESR study of decarboxylation. Chem. Mater. 1994; 6:1581-1586.
Krafft, et al. Chemistry, physical chemistry, and uses of molecular fluorocarbon—hydrocarbon diblocks, triblocks, and related compounds—unique "apolar" components for self-assembled colloid and interface engineering. Chem. Rev. 2009; 109:1714-1792.
Krafft, et al. Highly fluorinated amphiphiles and colloidal systems, and their applications in the biomedical field. A contribution. Biochimie. 1998: 80:489-514.
Lehmann, et al. Droplet-Based DNA purification in a Magnetic Lab-on-a-Chip. Angew Chem Int Ed Engl. May 5, 2006;45(19):3062-7.
Mazutis, et al. Selective droplet coalescence using microlfuidic systems. Lab Chip. Apr. 24, 2012;12(10):1800-6. doi: 10.1039/c21c40121e. Epub Mar. 27, 2012.

(Continued)

*Primary Examiner* — Jezia Riley
(74) *Attorney, Agent, or Firm* — Kolisch Hartwell, P.C.

(57) ABSTRACT

The present disclosure provides methods, devices, systems and compositions for detecting nucleic acids in polymerase chain reaction assays, such as droplet digital polymerase chain reaction (ddPCR) assays. The present disclosure provides methods, devices, systems and compositions for detecting nucleic acids in ddPCR assays using intercalating dyes. A dual surfactant system with at least one fluorosurfactant and at least one non-ionic non-fluorosurfactant may be employed for droplet generation and nucleic acid detection.

22 Claims, 19 Drawing Sheets

(56) References Cited

OTHER PUBLICATIONS

Spool, et al. Perfluoropolyethers: Analysis by TOF-SIMS. Macromolecules. 1996; 29:1691-1697.
Theberge, et al. Microfluidic platform for combinatorial synthesis in picolitre droplets. Lab Chip. Apr. 7, 2012;12(7):1320-6. doi: 10.1039/c2lc21019c. Epub Feb. 20, 2012.
Tonelli, et al. Perfluoropolyether functional oligomers: unusual reactivity in organic chemistry. Journal fo Flourine Chemistry. 2002; 118:107-121.
Zhu, et al. Synthesis and Self-Assembly of Highly Incompatible Polybutadiene-Poly(hexafluoropropylene oxide) Diblock Copolymers. Journal of Polymer Science. Part B: Polymer Physics. 2005; 43:3685-3694.

* cited by examiner

COMPOSITIONS, METHODS AND SYSTEMS FOR POLYMERASE CHAIN REACTION ASSAYS

CROSS-REFERENCE

This application claims the benefit of U.S. Provisional Application No. 61/775,415, filed Mar. 8, 2013, which application is incorporated herein by reference.

BACKGROUND

An assay is an investigative procedure for determining the presence, quantity, activity, and/or other properties or characteristics of components in a sample. Very often, the components of interest within a sample e.g., a nucleic acid, an enzyme, a virus, a bacterium are only minor constituents of the sample and may, therefore, be difficult to detect or quantify.

An example of a biological assay is a polymerase chain reaction (PCR) assay. Certain types of PCR can be quantitative in specific settings. For example, real-time PCR (which generally involves monitoring the progression of amplification using fluorescence probes) may permit quantification of target nucleic acids in a sample, particularly where the target nucleic acids are somewhat abundant.

Droplet digital polymerase chain reaction (ddPCR) is a popular tool for quantitative measurement of absolute DNA concentration. As opposed to the relative measurement obtained from the real-time PCR reactions, ddPCR enables absolute measurement of target deoxyribonucleic acid (DNA), ribonucleic acid (RNA) molecules. Absolute quantification is advantageous in several applications, such as measuring copy number variation, detecting rare sequences and mutations, and analyzing gene expression reaction.

SUMMARY

In an aspect, the present disclosure provides a method of generating a plurality of droplets. The method comprises providing an oil composition comprising an oil and a fluorosurfactant, providing an aqueous composition comprising a target nucleic acid, a non-ionic non-fluorosurfactant and an intercalating dye, and contacting the oil composition of with the aqueous composition, thereby generating a plurality of droplets suspended in a continuous phase. The fluorosurfactant can be selected from the group consisting of

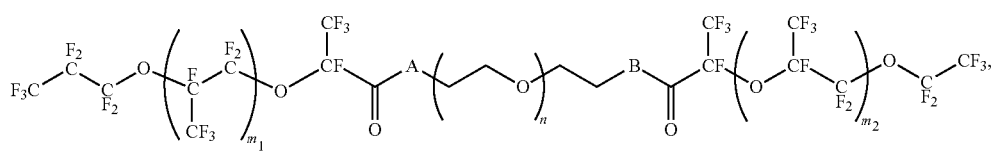

Formula I wherein each of A and B is oxygen (O) or $NR_1$, wherein $R_1$ is H or an alkyl group; each of $m_1$ and $m_2$ is a number from about 10 to 100; n is a number from about 10 to 60;

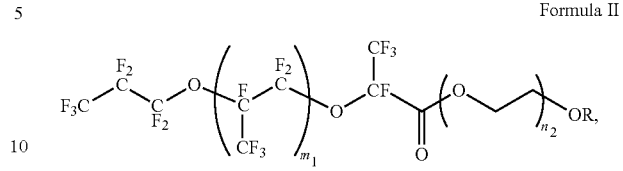

Formula II wherein $m_3$ is a number from about 20 to 50; $n_2$ is a number from about 8 to 30; and R is H or an alkyl group; and

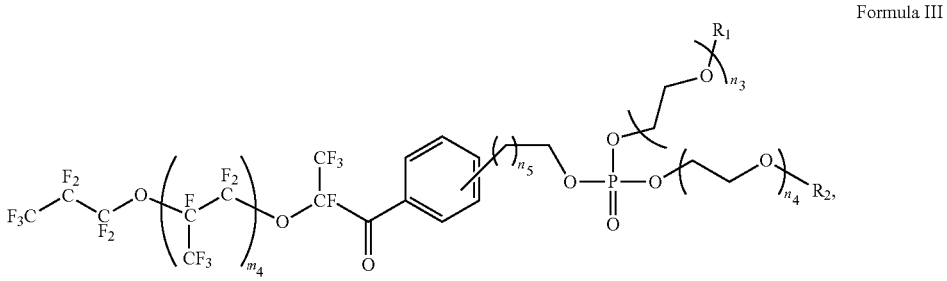

Formula III wherein $m_4$ is a number from about 20 to 50; each of $n_3$ and $n_4$ is a number from about 5 to 25; $n_5$ is a number from about 0 to 3; and each of $R_1$ and $R_2$ is an alkyl group or H. In some cases, the fluorosurfactant can be non-ionic. In some cases, the fluorosurfactant can comprise a mixture of Formula I, Formula II, and/or Formula III. For example, the fluorosurfactant can comprise a mixture of Formula I and Formula II. In some examples, the mixture can further comprise Formula XI:

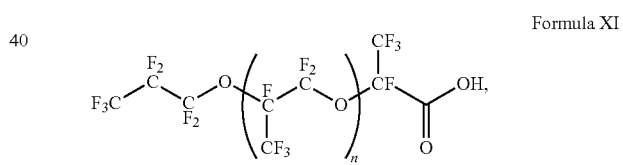

Formula XI wherein n is a number from about 10 to 100.

In some cases, the fluorosurfactant can have a purity of at least about 90% (w/w). For example, the fluorosurfactant can comprise at least about 90% (w/w) of a mixture of Formula I and Formula II. Further, the mixture of Formula I and Formula II can be in a ratio of at least about 90:10 (w/w). In some cases, fluorosurfactant mixture can comprise about 0.5% to 5% (w/w) of Formula XI. In certain cases, the oil formulation can comprise less than about 0.5% (w/w) of Formula XI.

In some cases, the method can further comprise thermally cycling the plurality of droplets to amplify the target nucleic acid and detecting the target nucleic acid. In some cases, the fluorosurfactant can be of Formula I. Each of A and B can be O. Each of $m_1$ and $m_2$ can be from about 20 to 40, and n can be from about 15 to 30. For example, each of $m_1$ and $m_2$ can be about 35 and n can be about 22. In certain cases, the fluorosurfactant can comprise a mixture of Formula I and Formula II. In some cases, the mixture can further comprise Formula XI. The fluorosurfactant can have a hydrophilic-lipophilic balance of at least about 0.5. The fluorosurfactant can have a hydrophilic-lipophilic balance of less than about 5.0. The fluorosurfactant can have a hydrophilic-lipophilic balance in a range from about 0.5 to 5.0. For example, the fluorosurfactant can have a hydrophilic-lipophilic balance of about 1.5.

The non-ionic non-fluorosurfactant can be a copolymer of ethylene oxide and propylene oxide. The non-ionic non-fluorosurfactant can be a triblock copolymer of polyethylene oxide-polyproylene oxide-polyethylene oxide. In some examples, the non-ionic non-fluorosurfactant can be Pluronic®. For example, the non-ionic non-fluorosurfactant can be Pluronic® F-98. The concentration of the Pluronic® F-98 can be in a range from about 0.1%-3% (weight percent).

The oil can comprise a fluorous oil. The fluorous oil can be 2-trifluoromethyl-3-ethoxydodeca-fluorohexane (HFE-7500) or 1,1,1,2,2,3,4,5,5,5-decafluoro-3-methoxy-4-(trifluoromethyl)pentane (HFE-7300). The intercalating dye can be EvaGreen® or SYBR® Green. The continuous phase can comprise the oil.

The plurality of droplets can be aqueous droplets encapsulated by the oil. In some cases, less than about 5% of the intercalating dye can be detected outside of the aqueous phase of the aqueous droplets after about 5 thermal cycles. In some cases, less than about 5% of the intercalating dye can be detected outside of the aqueous phase of the aqueous droplets after about 10 thermal cycles. In some cases, less than about 5% of the intercalating dye can be detected outside of the aqueous phase of the aqueous droplets after about 20 thermal cycles. In some cases less than about 5% of the intercalating dye can be detected outside of the aqueous phase of the aqueous droplets after about 50 thermal cycles. In some cases, less than about 5% of the intercalating dye can be detected outside of the aqueous phase of the aqueous droplets after about 100 thermal cycles.

In some cases, less than about 10% of the intercalating dye can be detected outside of the aqueous phase of the aqueous droplets after about 5 thermal cycles. In some cases, less than about 10% of the intercalating dye can be detected outside of the aqueous phase of the aqueous droplets after about 10 thermal cycles. In some cases, less than about 10% of the intercalating dye can be detected outside of the aqueous phase of the aqueous droplets after about 20 thermal cycles. In some cases, less than about 10% of the intercalating dye can be detected outside of the aqueous phase of the aqueous droplets after about 50 thermal cycles. In some cases, less than about 10% of the intercalating dye can be detected outside of the aqueous phase of the aqueous droplets after about 100 thermal cycles.

On average, each of the plurality of droplets can comprise less than $5.5 \times 10^{12}$ target nucleic acids after thermal cycling. The detecting can comprise measuring fluorescence from the intercalating dyes.

Another aspect of the present disclosure provides a droplet generator, comprising a first channel in fluid communication with a carrier fluid source and a second channel in fluid communication with a sample source. The first channel meets the second channel at an intersection. A droplet channel is in fluid communication with the intersection. During use, an emulsion comprising one or more droplets generated at the intersection flows along the droplet channel. The carrier fluid source comprises an oil and a fluorosurfactant. The fluorosurfactant can be selected from the group consisting of:

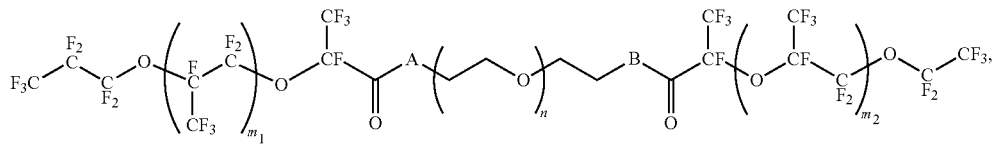

Formula I wherein each of A and B is oxygen (O) or $NR_1$, wherein $R_1$ is H or an alkyl group; each of $m_1$ and $m_2$ is a number from about 10 to 100; n is a number from about 10 to 60;

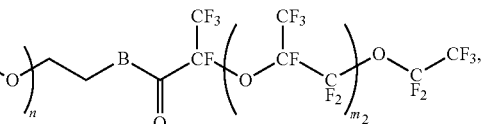

Formula II wherein $m_3$ is a number from about 20 to 50; $n_2$ is a number from about 8 to 30; R is H or an alkyl group; and

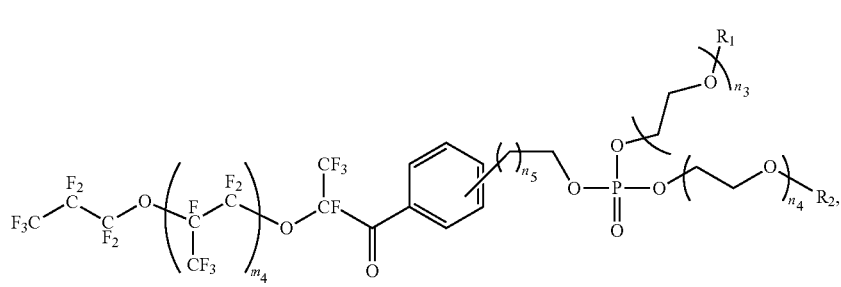

Formula III wherein $m_4$ is a number from about 20 to 50; each of $n_3$ and $n_4$ is a number from about 5 to 25; $n_5$ is a number from about 0 to 3; and each of $R_1$ and $R_2$ is an alkyl group or H. The sample source can comprise a target nucleic acid, a non-ionic non-fluorosurfactant and an intercalating dye. In some cases, the fluorosurfactant can be non-ionic. In some cases, the fluorosurfactant can be a mixture of Formula I, Formula II, and/or Formula III. For example, the fluorosurfactant can be a mixture of Formula I and Formula II. In some examples, the mixture can further comprise Formula XI:

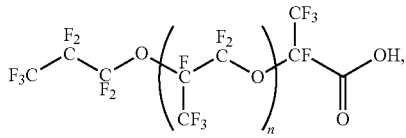

Formula XI wherein n is a number from about 10 to 100.

In some cases, the fluorosurfactant can have a purity of at least about 90% (w/w). For example, the fluorosurfactant can comprise at least 90% (w/w) of a mixture of Formula I and Formula II. Further, the mixture of Formula I and Formula II can be in a ratio of at least about 90:10 (w/w). In some cases, fluorosurfactant mixture can comprise about 0.5% to 5% (w/w) of Formula XI. In certain cases, the oil formulation can comprise less than about 0.5% (w/w) of Formula XI.

In another aspect, the present disclosure provides a composition, comprising a fluorosurfactant, a non-ionic non-fluorosurfactant and an intercalating dye. The fluorosurfactant can be selected from the group consisting of:

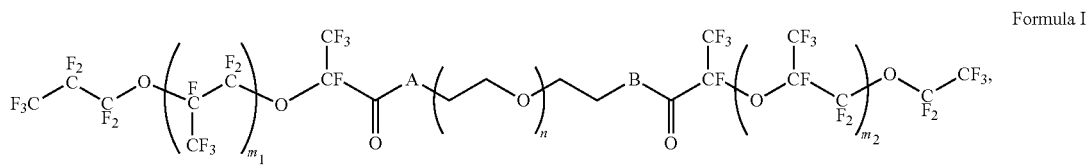

Formula I wherein each of A and B is oxygen (O) or $NR_1$, wherein $R_1$ is H or an alkyl group; each of $m_1$ and $m_2$ is a number from about 10 to 100; n is a number from about 10 to 60;

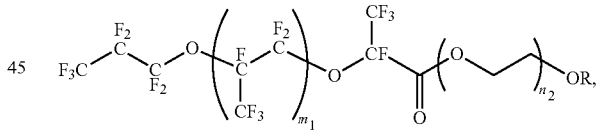

Formula II wherein $m_3$ is a number from about 20 to 50; $n_2$ is a number from about 8 to 30; R is H or an alkyl group; and Formula III

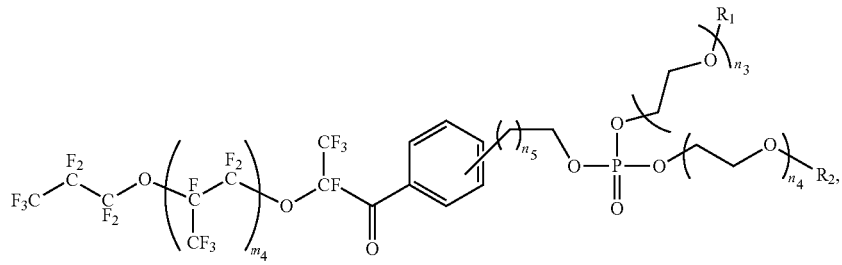

wherein $m_4$ is a number from about 20 to 50, each of $n_3$ and $n_4$ is a number from about 5 to 25, and $n_5$ is a number from about 0 to 3; and each of $R_1$ and $R_2$ is H or an alkyl group. In some cases, the fluorosurfactant can be non-ionic. In some cases, the fluorosurfactant can be a mixture of Formula I, Formula II, and/or Formula III. For example, the fluorosurfactant can be a mixture of Formula I and Formula II. In some examples, the mixture can further comprise Formula XI. In some cases, the fluorosurfactant can have a purity of at least about 90% (w/w). For example, the fluorosurfactant can comprise at least 90% (w/w) of a mixture of Formula I and Formula II. Further, the mixture of Formula I and Formula II can be in a ratio of at least about 90:10 (w/w). In some cases, fluorosurfactant mixture can comprise about 0.5% to 5% (w/w) of Formula XI. In certain cases, the oil formulation can comprise less than about 0.5% (w/w) of Formula XI.

In another aspect, the present disclosure provides a copolymer of Formula I wherein each of A and B is oxygen (O) or $NR_1$, wherein $R_1$ is H or an alkyl group, each of $m_1$ and $m_2$ is a number from about 10 to 100, and n is a number from about 10 to 60. In some cases, the copolymer can have a purity of at least about 90% 000.

of the features and advantages of the present invention will be obtained by reference to the following detailed description that sets forth illustrative embodiments, in which the principles of the invention are utilized, and the accompanying drawings of which:

FIG. 1 is a graphical representation of the dependence of the rate of leaching of the DNA intercalating dye on the concentration of carboxylic acid IV (Krytox® 157FS$_H$ (carboxylic acid XI) is used as a representative example);

FIG. 2 is a graphical representation of the normalized dye response with respect to time in carboxylic acid XI, fluorosurfactant XII and HFE-7500, in accordance with an embodiment of the present disclosure;

FIG. 3 illustrates the ion-pair mediated mechanism for dye leaching, with SYBR® Green as a representative DNA intercalating dye, in accordance with an embodiment of the present disclosure;

FIG. 4 is a graphical representation of coarse titration of surfactant I working concentration range, in accordance with an embodiment of the present disclosure;

FIG. 5 is a graphical representation of the effect of Pluronic® type and concentration on droplet stability, in accordance with an embodiment of the present disclosure;

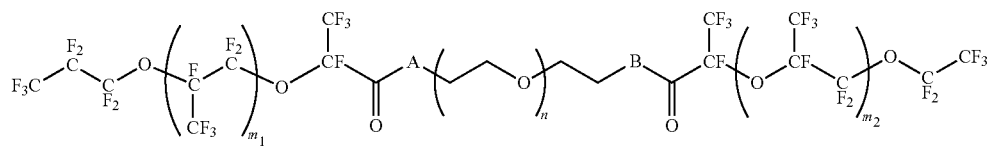

Formula I

In another aspect, the present disclosure provides a method of synthesizing a copolymer. The method comprises heating a solution of perfluoropolyether carboxylic acid in a first fluorous oil in the presence of oxalyl chloride and a catalytic amount of dimethylformate (DMF) to form an acid chloride. Next, the acid chloride can be reacted with polyethylene glycol in a solvent comprising a second fluorous oil and an ether in the presence of an amine to form a product mixture comprising a perfluoropolyether-containing copolymer, wherein the amount of the polyethylene glycol is about ½ equivalent of the acid chloride. The perfluoropolyether-containing copolymer can then be separated from the product mixture.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding

DETAILED DESCRIPTION

Figure 1:
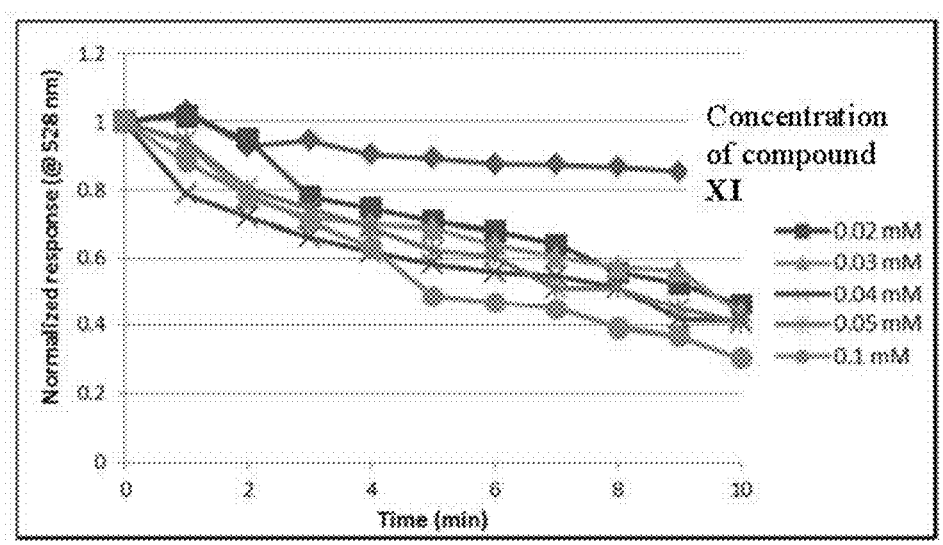

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention.

The present disclosure provides devices, systems, methods and compositions for using nucleic acid intercalating dyes in polymerase chain reaction assays, such as, for example, droplet digital polymerase chain reaction (ddPCR) assays. Devices, systems, methods and compositions of the disclosure can be employed for use with various types of nucleic acids, such as deoxyribonucleic acid (DNA), ribonucleic acid (RNA), and variants thereof. The devices, systems, methods and compositions of the disclosure may prevent, reduce or inhibit the leaching of the intercalating dyes from the aqueous droplets into the continuous phase during PCR assays (also "dye leaching" herein). In general, the present disclosure described herein pertains to a dual phase surfactant system which enables the application of fluorescent intercalating dyes, in addition to Taqman probes, for use in PCR assays.

In some embodiments, the dual phase system is an oil phase comprising a fluorosurfactant and an aqueous phase comprising a non-ionic non-fluorosurfactant. In some cases the oil is a fluorous oil, the fluorosurfactant is a triblock polymer of Formula I, and the aqueous phase is a buffered solution of the triblock polymer PEG-PPG-PEG of Formula VI. In some cases, the fluorosurfactant can be non-ionic. In some cases, the fluorosurfactant can comprise a mixture of Formula I, Formula II, and/or Formula III. For example, the fluorosurfactant can comprise a mixture of Formula I and Formula II. In certain examples, the mixture can further comprise Formula XI.

In an aspect, the present disclosure provides synthetic methods to obtain high purity fluorosurfactants. These high purity fluorosurfactants may allow sufficient quantities of intercalating dye to be maintained within droplets during droplet generation, thermal cycling, and droplet interrogation workflow. The high purity fluorosurfactants obtained herein may also facilitate a better or otherwise improved understanding of the mechanism of dye leaching phenomenon.

The unexpected realization of the mechanism behind dye leaching, coupled with the methods for production of high-purity fluorosurfactants, provide a systematic solution to a critical shortcoming of ddPCR assays. The micro-emulsion comprising the specific combination of continuous phase and aqueous phase described herein provide non-ionic stabilized droplets for the application of DNA intercalating dyes in ddPCR assays.

Methods of Making Fluorosurfactants

In an aspect, the present disclosure provides methods of synthesizing a perfluoropolyether-containing fluorosurfactant. Scheme 1 shows a representative fluorosurfactant XII of the present disclosure and an exemplary carboxylic acid XI starting material.

Scheme 1

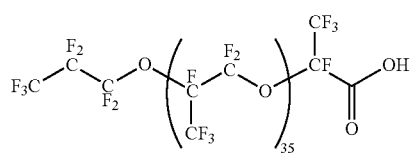

XI

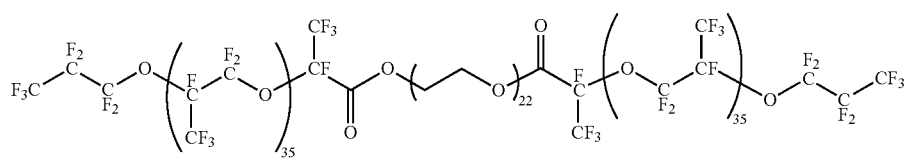

XII

A method for forming a perfluoropolyether-containing fluorosurfactant comprises (a) heating a solution of perfluoropolyether carboxylic acid in a fluorous oil in the presence of oxalyl chloride to form an acid chloride, such as perfluoropolyether acid chloride; (b) reacting the acid chloride with a polyethylene glycol to form a product mixture comprising perfluoropolyether-containing fluorosurfactant; and (c) separating the perfluoropolyether-containing fluorosurfactant from the product mixture to provide a fluorosurfactant product. These synthetic operations are summarized in Scheme 2 (see below) for the fluorosurfactant X as a representative example.

Scheme 2

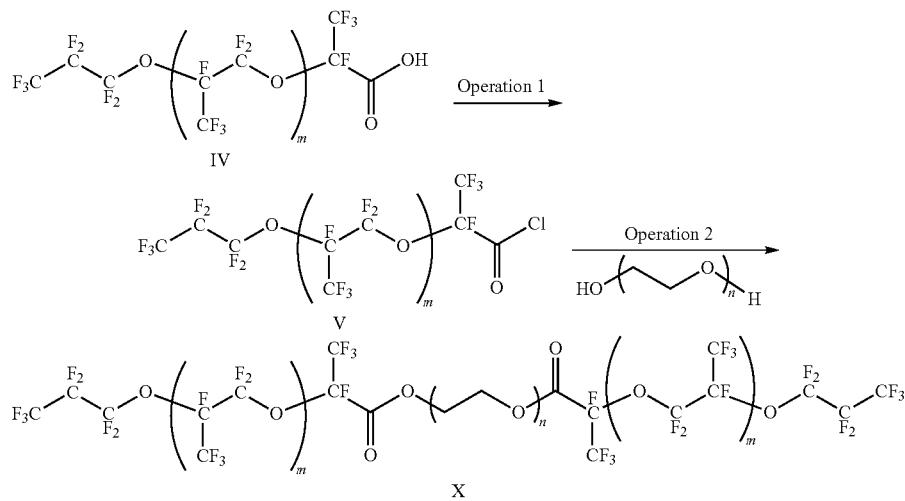

Operation 1

The conversion of perfluoropolyether carboxylic acid starting material to perfluoropolyether acid chloride can be achieved using a variety of reagents. In some cases this conversion is achieved by treating perfluoropolyether carboxylic acid with oxalyl chloride ($C_2O_2Cl_2$). In other cases, the conversion can be achieved by reaction of perfluoropolyether carboxylic acid with thionyl chloride ($SOCl_2$). In yet other cases, phosphorous pentachloride ($PCl_5$) or phosphorous tri chloride ($PCl_3$) are used to accomplish this transformation. In some cases, the conversion of the carboxylic acid starting material to the corresponding acid chloride is achieved by reaction with carbon tetrachloride and triphenyl phosphine ($PPh_3$). In some cases the transformation is achieved by reaction with cyanuric chloride ($C_3N_3Cl_3$).

In some cases the amount of reagent used for the conversion of the carboxylic acid starting material to the acid chloride product is in the range of about 0.1 equivalents (equiv) to 100 equiv, or about 1.0 equiv to 10.0 equiv. In some cases the amount of reagent used is in the range of about 1.0 equiv-2.0 equiv, about 1.0 equiv-3.0 equiv, about 1.0 equiv-4.0 equiv, about 1.0 equiv-5.0 equiv, about 1.0 equiv-6.0 equiv, about 1.0 equiv-7.0 equiv, about 1.0 equiv-8.0 equiv, about 1.0 equiv-9.0 equiv, about 2.0 equiv-3.0 equiv, about 2.0 equiv-4.0 equiv, about 2.0 equiv-5.0 equiv, about 2.0 equiv-6.0 equiv, about 2.0 equiv-7.0 equiv, about 2.0 equiv-8.0 equiv, about 2.0 equiv-9.0 equiv, about 2.0 equiv-10.0 equiv, about 3.0 equiv-4.0 equiv, about 3.0 equiv-5.0 equiv, about 3.0 equiv-6.0 equiv, about 3.0 equiv-7.0 equiv, about 3.0 equiv-8.0 equiv, about 3.0 equiv-9.0 equiv, about 3.0 equiv-10.0 equiv, about 4.0 equiv-5.0 equiv, about 4.0 equiv-6.0 equiv, about 4.0 equiv-7.0 equiv, about 4.0 equiv-8.0 equiv, about 4.0 equiv-9.0 equiv, about 4.0 equiv-10.0 equiv, about 5.0 equiv-6.0 equiv, about 5.0 equiv-7.0 equiv, about 5.0 equiv-8.0 equiv, about 5.0 equiv-9.0 equiv, about 5.0 equiv-10.0 equiv, about 6.0 equiv-7.0 equiv, about 6.0 equiv-8.0 equiv, about 6.0 equiv-9.0 equiv, about 6.0 equiv-10.0 equiv, about 7.0 equiv-8.0 equiv, about 7.0 equiv-9.0 equiv, about 7.0 equiv-10.0 equiv, about 8.0 equiv-9.0 equiv, about 8.0 equiv-10.0 equiv, or about 9.0 equiv-10.0 equiv. In some cases the amount of reagent used is at least about 1.0, about 1.5 equiv, about 2.0 equiv, about 2.5 equiv, about 3.0 equiv, about 3.5 equiv, about 4.0 equiv, about 4.5 equiv, about 5.0 equiv, about 5.5 equiv, about 6.0 equiv, about 6.5 equiv, about 7.0 equiv, about 7.5 equiv, about 8.0 equiv, about 8.5 equiv, about 9.0 equiv, about 9.5 equiv, or about 10.0 equiv. In some cases the conversion of the carboxylic acid to the acid chloride is accomplished by treatment with about 5.0 equiv of oxalyl chloride.

In some cases, conversion of carboxylic acid to the corresponding acid chloride is carried out in a fluorous solvent. In some cases the solvent is the perfluoroalkyl ether. In some cases the perfluoroalkyl ether is methyl nanofluorobutyl ether (HFE-7100), 1,1,1,2,2,3,4,5,5,5-decafluoro-3-methoxy-4-(trifluoromethyl)pentane (HFE-7300), or 3-ethoxy-1,1,1,2,3,4,4,5,5,6,6,6-dodecafluoro-2-trifluoromethyl-hexane (HFE-7500).

In some cases, conversion of the carboxylic acid to the acid chloride is further facilitated by adding a reaction catalyst. A catalyst is a substance, in some cases used in small amounts relative to the reactants, that increases or otherwise modifies the rate of a reaction without being appreciably consumed in the process. In some cases the formation of the acid chloride is achieved by reaction with thionyl chloride or oxalyl chloride and dimethylformamide (DMF) is added as a reaction catalyst. In some cases the amount of catalyst used is in the range of about 0.001 equiv to 10 equiv, or about 0.01 equiv to 1.0 equiv. In some cases the amount of catalyst used is in the range of about 0.01 equiv-0.10 equiv, about 0.01 equiv-0.20 equiv, about 0.01 equiv-0.30 equiv, about 0.01 equiv-0.40 equiv, about 0.01 equiv-0.50 equiv, about 0.01 equiv-0.60 equiv, about 0.01 equiv-0.70 equiv, about 0.01 equiv-0.80 equiv, about 0.01 equiv-0.90 equiv, about 0.1 equiv-0.20 equiv, about 0.1 equiv-0.30 equiv, about 0.1 equiv-0.4 equiv, about 0.1 equiv-0.5 equiv, about 0.1 equiv-0.6 equiv, about 0.1 equiv-0.7 equiv, about 0.1 equiv-0.8 equiv, about 0.1 equiv-0.9 equiv, about 0.1 equiv-1.0 equiv, about 0.2 equiv-0.3 equiv, about 0.2 equiv-0.4 equiv, about 0.2 equiv-0.5 equiv, about 0.2 equiv-0.6 equiv, about 0.2 equiv-0.7 equiv, about 0.2 equiv-0.8 equiv, about 0.2 equiv-0.9 equiv, about 0.2 equiv-1.0 equiv, about 0.3 equiv-0.4 equiv, about 0.3 equiv-0.5 equiv, about 0.3 equiv-0.6 equiv, about 0.3 equiv-0.7 equiv, about 0.3 equiv-0.8 equiv, about 0.3 equiv-0.9 equiv, about 0.3 equiv-1.0 equiv, about 0.4 equiv-0.5 equiv, about 0.4 equiv-0.6 equiv, about 0.4 equiv-0.7 equiv, about 0.4 equiv- 0.8 equiv, about 0.4 equiv-0.9 equiv, about 0.4 equiv-1.0 equiv, about 0.5 equiv-0.6 equiv, about 0.5 equiv-0.7 equiv, about 0.5 equiv-0.8 equiv, about 0.5 equiv-0.9 equiv, about 0.5 equiv-1.0 equiv, about 0.6 equiv-0.7 equiv, about 0.6 equiv-0.8 equiv, about 0.6 equiv-0.9 equiv, about 0.6 equiv-1.0 equiv, about 0.7 equiv-0.8 equiv, about 0.7 equiv-0.9 equiv, about 0.7 equiv-1.0 equiv, about 0.8 equiv-0.9 equiv, about 0.8 equiv-1.0 equiv, or about 0.9 equiv-1.0 equiv. In some cases the amount of the catalyst used in the range of about 0.01 equiv-0.02 equiv, about 0.01 equiv-0.03 equiv, about 0.01 equiv-0.04 equiv, about 0.01 equiv-0.05 equiv, about 0.01 equiv-0.06 equiv, about 0.01 equiv-0.07 equiv, about 0.01 equiv-0.08 equiv, or about 0.01 equiv-0.09 equiv. In some cases the conversion of the carboxylic acid to the acid chloride is accomplished by treatment with about 5.0 equiv of oxalyl chloride in HFE-7100 and is facilitated by addition of about 0.05 equiv of DMF.

In some cases, formation of the acid chloride is accomplished at room temperature. As an alternative, the reaction is conducted at an elevated temperature. In some cases the reaction is carried out by heating or refluxing the reaction mixture at the temperature in the range of about 40° C.-80° C. In some cases the reaction is performed at a temperature in the range of about 40° C.-45° C., about 40° C.-50° C., about 40° C.-55° C., about 40° C.-60° C., about 40° C.-65° C., about 40° C.-70° C., about 40° C.-75° C., about 40° C.-80° C., about 50° C.-55° C., about 50° C.-60° C., about 50° C.-65° C., about 50° C.-70° C., about 50° C.-75° C., about 50° C.-80° C., about 60° C.-65° C., about 60° C.-70° C., about 60° C.-75° C., about 60° C.-80° C., about 70° C.-75° C., about 70° C.-80° C., or about 75° C.-80° C. In some cases the reaction temperature is about 40° C., about 45° C., about 50° C., about 55° C., about 60° C., about 65° C., about 70° C., about 75° C., about 80° C.

The reaction time for conversion of the carboxylic acid starting material to the corresponding acid chloride intermediate is in the range of about 0.5 hours (h)-12 h. In some cases the reaction is allowed to run for a period of about 1 h-12 h, about 2 h-12 h, about 3 h-12 h, about 4 h-12 h, about 5 h-12 h, about 6 h-12 h, about 7 h-12 h, about 8 h-12 h, about 9 h-12 h, about 0.5 h-11 h, about 1 h-11 h, about 2 h-11 h, about 3 h-11 h, about 4 h-11 h, about 5 h-11 h, about 6 h-11 h, about 7 h-11 h, about 8 h-11 h, about 9 h-11 h, about 10 h-11 h, about 0.5 h-10 h, 1 h-10 h, about 2 h-10 h, about 3 h-10 h, about 4 h-10 h, about 5 h-10 h, about 6 h-10 h, about 7 h-10 h, about 8 h-10 h, about 9 h-10 h, about 0.5 h-9 h, about 1 h-9 h, about 2 h-9 h, about 3 h-9 h, about 4 h-9 h, about 5 h-9 h, about 6 h-9 h, about 7 h-9 h, about 8 h-9 h, about 0.5 h-8 h, about 1 h-8 h, about 2 h-8 h, about 3 h-8 h, about 4 h-8 h, about 5 h-8 h, about 6 h-8 h, about 7 h-8 h, 0.5 h-7 h, about 1 h-7 h, about 2 h-7 h, about 3 h-7 h, about 4 h-7 h, about 5 h-7 h, about 6 h-7 h, about 0.5 h-6 h, about 1 h-6 h, about 2 h-6 h, about 3 h-6 h, about 4 h-6 h, about 5 h-6 h, about 0.5 h-5 h, about 1 h-5 h, about 2 h-5 h, about 3 h-5 h, about 4 h-5 h, about 0.5 h-4 h, about 1 h-4 h, about 2 h-4 h, about 3 h-4 h, about 0.5 h-3 h, about 1 h-3 h, about 2 h-3 h, about 0.5 h-2 h, about 1 h-2 h, or about 0.5 h-1 h. In some cases the reaction is allowed to run for a period of about 1 h, about 2 h, about 3 h, about 4 h, about 5 h, about 6 h, about 7 h, about 8 h, about 9 h, about 10 h, about 11 h or about 12 h.

In some examples, the conversion of the carboxylic acid to the acid chloride is achieved by reaction with about 5.0 equiv of oxalyl chloride and about 0.05 equiv of DMF as catalyst in HFE-7100 for about 4 h at about 60° C.

In some cases the formation of the acid chloride is performed under an inert atmosphere to ensure that the acid chloride product V does not revert back to the carboxylic acid starting material IV. In some cases the inert atmosphere is obtained by purging the reaction flask with an inert gas. In some cases the inert gas is nitrogen or argon.

In some cases the conversion of the carboxylic acid to the acid chloride is achieved by reaction with about 5.0 equiv of acid chloride and about 0.05 equiv of DMF as catalyst in HFE-7100 for about 4 h at about 60° C. under nitrogen atmosphere.

The acid chloride obtained from this reaction can be used in the next operation immediately or shortly after it is prepared to prevent any degradation or hydrolysis back to the carboxylic acid starting material. In some cases the acid chloride is stored for a time period of about 5 minutes (min)-12 hour ("h") before being used in the next operation. In some cases the acid chloride is stored for a period of about 30 min-12 h, about 1 h-12 h, about 1 h-12 h, about 2 h-12 h, about 3 h-12 h, about 4 h-12 h, about 5 h-12 h, about 6 h-12 h, about 7 h-12 h, about 8 h-12 h, about 9 h-12 h, about 10 h-12 h, about 11 h-12 h, about 5 min-11 h, 30 min-11 h, about 1 h-11 h, about 1 h-11 h, about 2 h-11 h, about 3 h-11 h, about 4 h-11 h, about 5 h-11 h, about 6 h-11 h, about 7 h-11 h, about 8 h-11 h, about 9 h-11 h, about 10 h-11 h, about 5 min-10 h, 30 min-10 h, about 1 h-10 h, about 2 h-10 h, about 3 h-10 h, about 4 h-10 h, about 5 h-10 h, about 6 h-10 h, about 7 h-10 h, about 8 h-10 h, about 9 h-10 h, about 5 min-9 h, 30 min-9 h, about 1 h-9 h, about 2 h-9 h, about 3 h-9 h, about 4 h-9 h, about 5 h-9 h, about 6 h-9 h, about 7 h-9 h, about 8 h-9 h, 5 min-8 h, 30 min-8 h, about 1 h-8 h, about 2 h-8 h, about 3 h-8 h, about 4 h-8 h, about 5 h-8 h, about 6 h-8 h, about 7 h-8 h, 5 min-7 h, 30 min-7 h, about 1 h-7 h, about 2 h-7 h, about 3 h-7 h, about 4 h-7 h, about 5 h-7 h, about 6 h-7 h, about 5 min-6 h, 30 min-6 h, about 1 h-6 h, about 2 h-6 h, about 3 h-6 h, about 4 h-6 h, about 5 h-6 h, about 5 min-5 h, 30 min-5 h, about 1 h-5 h, about 2 h-5 h, about 3 h-5 h, about 4 h-5 h, about 5 min-4 h, 30 min-4 h, about 1 h-4 h, about 2 h-4 h, about 3 h-4 h, about 5 min-3 h, 30 min-3 h, about 1 h-3 h, about 2 h-3 h, about 5 min-2 h, 30 min-2 h, about 1 h-2 h, about 5 min-1 h, or about 30 min-1 h before being used in the next operation. In some cases the acid chloride is stored for a period of about 5 min, about 10 min, about 15 min, about 20 min, about 25 min, about 30 min, about 35 min, about 40 min, about 45 min, about 50 min, about 55 min, about 1.0 h, about 1.5 h, about 2.0 h, about 2.5 h, about 3.0 h, about 3.5 h, about 4.0 h, about 4.5 h, about 5.0 h, about 5.5 h, about 6.0 h, about 6.5 h, about 7.0 h, about 7.5 h, about 8.0 h, about 8.5 h, about 9.0 h, about 9.5 h, about 10.0 h, about 10.5 h, about 11.0 h, about 11.5 h, or about 12 h prior to use in the next operation.

Operation 2

Upon formation of perfluoropolyether acid chloride, the perfluoropolyether acid chloride can be coupled to polyethylene glycol (PEG) to form a perfluoropolyether-containing fluorosurfactant. The coupling of the acid chloride with PEG can be achieved by reaction of the acid chloride with PEG, in some cases in the presence of an organic base. In some examples, at least about 0.1 equiv, about 0.2 equiv, about 0.3 equiv, about 0.4 equiv, about 0.5 equiv, about 0.6 equiv, about 0.7 equiv, about 0.8 equiv, about 0.9 equiv, about 1 equiv, about 2 equiv, about 3 equiv, about 4 equiv, about 5 equiv, or about 10 equiv of PEG is used. In some cases the organic base is a tertiary amine. In an example, the amine is triethylamine. In another example, the amine is diisopropylethylamine. In some cases the amount of amine used is in the range of 1.0 equiv-5.0 equiv. In some cases the amount of amine used is in the range of about 1.0 equiv-2.0 equiv, about 1.0 equiv-2.5 equiv, about 1.0 equiv-3.0 equiv, about 1.0 equiv-3.5 equiv, about 1.0 equiv-4.0 equiv, about 1.0 equiv-4.5 equiv, about 1.0 equiv-5.0 equiv, about 1.5 equiv-2.0 equiv, about 1.5 equiv-2.5 equiv, about 1.5 equiv-3.0 equiv, about 1.5 equiv-3.5 equiv, about 1.5 equiv-4.0 equiv, about 1.5 equiv-4.5 equiv, about 1.5 equiv-5.0 equiv, about 2.0 equiv-2.5 equiv, about 2.0 equiv-3.0 equiv, about 2.0 equiv-3.5 equiv, about 2.0 equiv-4.0 equiv, about 2.0 equiv-4.5 equiv, about 2.0 equiv-5.0 equiv, about 2.5 equiv-3.0 equiv, about 2.5 equiv-3.5 equiv, about 2.5 equiv-4.0 equiv, about 2.5 equiv-4.5 equiv, about 2.5 equiv-5.0 equiv, about 3.0 equiv-4.0 equiv, about 3.0 equiv-4.5 equiv, about 3.0 equiv-5.0 equiv, about 3.5 equiv-4.0 equiv, about 3.5 equiv-4.5 equiv, about 3.5 equiv-5.0 equiv, about 4.0 equiv-4.5 equiv, about 4.0 equiv-4.5 equiv, about 4.0 equiv-4.0 equiv, or about 4.5 equiv-5.0 equiv. In some cases the amount of amine used that is used is at least about 1.0 equiv, about 1.5 equiv, about 2.0 equiv, about 2.5 equiv, about 3.0 equiv, about 3.5 equiv, about 4.0 equiv, about 4.5 equiv or about 5.0 equiv. In some examples, about 2.0 equiv of triethylamine is used.

In some cases, coupling of the perfluoropolyether acid chloride with PEG is carried out in a fluorous solvent. In some cases the solvent is the perfluoroalkyl ether. In some cases the perfluoroalkyl ether is methyl nonafluorobutyl ether (HFE-7100), 1,1,1,2,2,3,4,5,5,5-decafluoro-3-methoxy-4-(trifluoromethyl)pentane (HFE-7300), or 3-ethoxy-1,1,1,2,3,4,4,5,5,6,6,6-dodecafluoro-2-trifluoromethyl-hexane (HFE-7500). In some cases the fluorous solvent is mixed with a second non-fluorous solvent. In some cases the second non-fluorous solvent is organic ether solvent. In some cases the second solvent is diethyl ether, tetrahydrofuran (THF), dichloromethane (DCM), methyl tetrahydrofuran and dioxane.

In some cases the ratio of the fluorous solvent to the second non-fluorous solvent is in the range of about 10:1 to about 1:10. In some cases the ratio of the fluorous solvent to the second non-fluorous solvent is about 10:1 to about 1:1. In some cases the ratio of the fluorous solvent to the second non-fluorous solvent is at least about 10:1, at least about 9:1, at least about 8:1, at least about 7:1, at least about 6:1, at least about 5:1, at least about 4:1, at least about 3:1, at least about 2:1, or at least about 1:1. In some cases the ratio of the fluorous solvent to the second non-fluorous solvent is about 1:1 to about 1:10. In some cases the ratio of the fluorous solvent to the second non-fluorous solvent is at least about 1:2, at least about 1:3, at least about 1:4, at least about 1:5, at least about 1:6, at least about 1:7, at least about 1:8, at least about 1:9, or at least about 1:10. In some examples, the coupling of the acid chloride intermediate with 0.5 equiv PEG is carried out in a 2:1 mixture of HFE-7100 and THF.

In some cases coupling of the perfluoropolyether acid chloride and PEG is accomplished at room temperature. As an alternative, the coupling reaction may be conducted at an elevated temperature. In some cases the reaction is carried out by heating or refluxing the reaction mixture at the temperature in the range of about 40° C.-80° C. In some cases the reaction is performed at a temperature in the range of about 40° C.-45° C., about 40° C.-50° C., about 40° C.-55° C., about 40° C.-60° C., about 40° C.-65° C., about 40° C.-70° C., about 40° C.-75° C., about 40° C.-80° C., about 50° C.-55° C., about 50° C.-60° C., about 50° C.-65° C., about 50° C.-70° C., about 50° C.-75° C., about 50° C.-80° C., about 60° C.-65° C., about 60° C.-70° C., about 60° C.-75° C., about 60° C.-80° C., about 70° C.-75° C., about 70° C.-80° C., or about 75° C.-80° C. In some cases the reaction temperature is about 40° C., about 45° C., about 50° C., about 55° C., about 60° C., about 65° C., about 70° C., about 75° C. or about 80° C.

The reaction time for the coupling of the acid chloride and PEG can be from about 0.1 h to 100 h, or about 1 h to 50 h. In some cases the reaction is allowed to run for about 5 h-50 h, 10 h-50 h, 15 h-50 h, 20 h-50 h, 25 h-50 h, 30 h-50 h, 35 h-50 h, 40 h-50 h, 45 h-50 h, 5 h-40 h, 10 h-40 h, 15 h-40 h, 20 h-40 h, 25 h-40 h, 30 h-40 h, 35 h-40 h, 40 h-40 h, 5 h-30 h, 10 h-30 h, 15 h-30 h, 20 h-30 h, 25 h-30 h, 5 h-20 h, 10 h-20 h, 15 h-20 h, or 5 h-10 h.

In some cases the coupling of the acid chloride intermediate with half equiv of PEG is accomplished in about 2:1 mixture of HFE-7100 and THF with about 2.0 equiv of triethylamine at about 60° C. for about 18 h.

Upon formation of a product mixture (or crude product) comprising a perfluoropolyether-containing fluorosurfactant, the perfluoropolyether-containing fluorosurfactant can be separated from the crude product to yield a higher purity perfluoropolyether-containing fluorosurfactant product. In some cases the purification of the fluorosurfactant product may be performed by transferring the crude product into a separating funnel and dissolving it into a fluorous solvent. The fluorous solvent may be HFE-7100, HFE-7300 or HFE-7500. The unreacted PEG and the HCl salt of the amine (for, e.g., $NEt_3$.HCl, if triethylamine is used as a base) may precipitate out during the dissolution of the crude product in fluorous solvent and float to the top of the separation funnel. These are filtered out and the fluorous solvent is subsequently removed to obtain the high purity fluorosurfactants.

In some cases, the solution of the crude product in fluorous solvent may be allowed to stand for a period of about 30 min-24 h to allow all the unreacted PEG and HCl salt of the amine to precipitate out. In some cases the solution of the crude product in a fluorous solvent is allowed to stand for a time period of about 5 min-12 h before being filtered. In some cases the solution of the crude product in a fluorous solvent is allowed to stand for a period of about 30 min-12 h, about 1 h-12 h, about 1 h-12 h, about 2 h-12 h, about 3 h-12 h, about 4 h-12 h, about 5 h-12 h, about 6 h-12 h, about 7 h-12 h, about 8 h-12 h, about 9 h-12 h, about 10 h-12 h, about 11 h-12 h, about 5 min-11 h, 30 min-11 h, about 1 h-11 h, about 1 h-11 h, about 2 h-11 h, about 3 h-11 h, about 4 h-11 h, about 5 h-11 h, about 6 h-11 h, about 7 h-11 h, about 8 h-11 h, about 9 h-11 h, about 10 h-11 h, about 5 min-10 h, 30 min-10 h, about 1 h-10 h, about 2 h-10 h, about 3 h-10 h, about 4 h-10 h, about 5 h-10 h, about 6 h-10 h, about 7 h-10 h, about 8 h-10 h, about 9 h-10 h, about 5 min-9 h, 30 min-9 h, about 1 h-9 h, about 2 h-9 h, about 3 h-9 h, about 4 h-9 h, about 5 h-9 h, about 6 h-9 h, about 7 h-9 h, about 8 h-9 h, 5 min h-8 h, 30 min h-8 h, about 1 h-8 h, about 2 h-8 h, about 3 h-8 h, about 4 h-8 h, about 5 h-8 h, about 6 h-8 h, about 7 h-8 h, 5 min-7 h, 30 min-7 h, about 1 h-7 h, about 2 h-7 h, about 3 h-7 h, about 4 h-7 h, about 5 h-7 h, about 6 h-7 h, about 5 min-6 h, 30 min-6 h, about 1 h-6 h, about 2 h-6 h, about 3 h-6 h, about 4 h-6 h, about 5 h-6 h, about 5 min-5 h, 30 min-5 h, about 1 h-5 h, about 2 h-5 h, about 3 h-5 h, about 4 h-5 h, about 5 min-4 h, 30 min-4 h, about 1 h-4 h, about 2 h-4 h, about 3 h-4 h, about 5 min-3 h, 30 min-3 h, about 1 h-3 h, about 2 h-3 h, about 5 min-2 h, 30 min-2 h, about 1 h-2 h, about 5 min-1 h, or about 30 min-1 h before being used in the next operation (e.g., separation). In some cases the solution of the crude product in a fluorous solvent is allowed to stand for a period of about 5 min, about 10 min, about 15 min, about 20 min, about 25 min, about 30 min, about 35 min, about 40 min, about 45 min, about 50 min, about 55 min, about 1.0 h, about 1.5 h, about 2.0 h, about 2.5 h, about 3.0 h, about 3.5 h, about 4.0 h, about 4.5 h, about 5.0 h, about 5.5 h, about 6.0 h, about 6.5 h, about 7.0 h, about 7.5 h, about 8.0 h, about 8.5 h, about 9.0 h, about 9.5 h, about 10.0 h, about 10.5 h, about 11.0 h, about 11.5 h, or about 12 h prior to being filtered. In some further cases the of the crude product in a fluorous solvent is allowed to stand for a period of about 13 h, about 14 h, about 15 h, about 16 h, about 17 h, about 18 h, about 19 h, about 20 h, about 21 h, about 22 h, about 23 h, or about 24 h.

The purity of the fluorosurfactant can be assayed by numerous analytical techniques including but not limited to $^{19}$F NMR, $^{1}$H NMR, $^{13}$C NMR, FTIR, elemental analysis and a variety of fluorescence techniques Of particular interest is the resonance due to the carbonyl carbon (C=O) in the $^{13}$C spectrum of product I (~157 ppm), this resonance has undergone a significant up-field shift when compared to the carbonyl carbon of the carboxylic acid present in the carboxylic acid starting material (~162 ppm). In the $^{13}$C NMR spectrum of the purified product, a relatively weak resonance present at about present at 157±2 ppm may be assigned to the carbonyl carbons (C=O) of the two ester linkages, while the resonance due to the carbonyl carbon (COOH) of the carboxylic acid starting material IV observed at 162±2 ppm must be absent from the spectrum.

Dye Leaching

The use of common DNA intercalating dyes in ddPCR system is currently difficult due to the leaching of the intercalating dyes from within the droplet (aqueous phase) into the continuous (or oil) phase. In some situations, a decreased response in droplet fluorescence is observed over time, while the background fluorescence increases. A system that enables the use of DNA intercalating dyes in ddPCR reactions, while minimizing the dye leaching, may advantageously enable convenient and economical use of ddPCR assays. Thus, recognized herein is a need of a dual phase system that enables the application of fluorescent DNA dyes for use in ddPCR assays.

The present disclosure provides a mechanism for the dye-leaching phenomenon observed during the use of DNA intercalating dyes in ddPCR assays. This migration of the intercalating dyes from the aqueous phase droplets to the continuous phase has generally been described as micelle mediated transport or as passive diffusion. Applicants have recognized that dye leaching may be unexpectedly due to the presence of residual carboxylic acid material during the synthesis of surfactant. Without being bound by theory, a majority of the fluorosurfactants used in ddPCR assays are synthesized from carboxylic acid terminated starting materials. Inefficient conversion of the carboxylic acid starting material to the corresponding ester, amide or alternate carbonyl compound may result in unconverted carboxylic acid as being present as impurity in the fluorosurfactant. As depicted in FIG. 1, the amount of dye leaching is found to increase with the amount of the unreacted carboxylic acid impurity in the fluorosurfactant.

Figure 2:
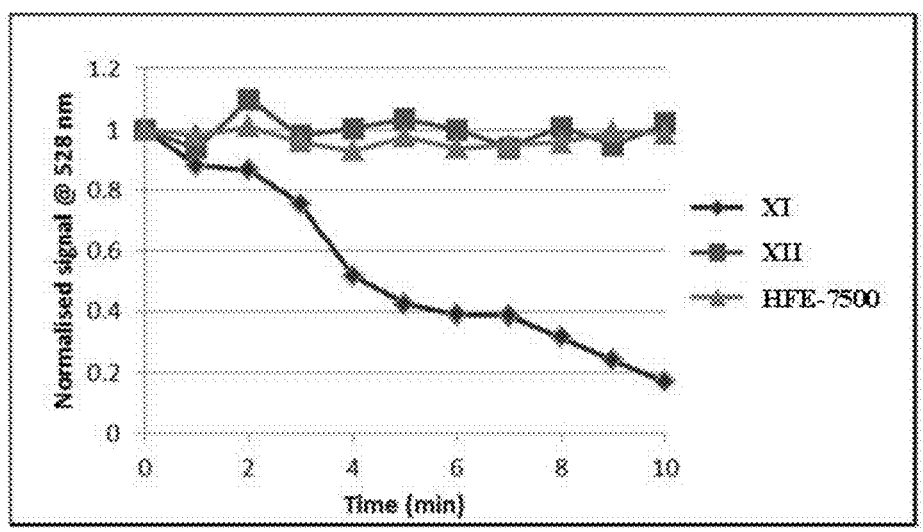
Figure 3:
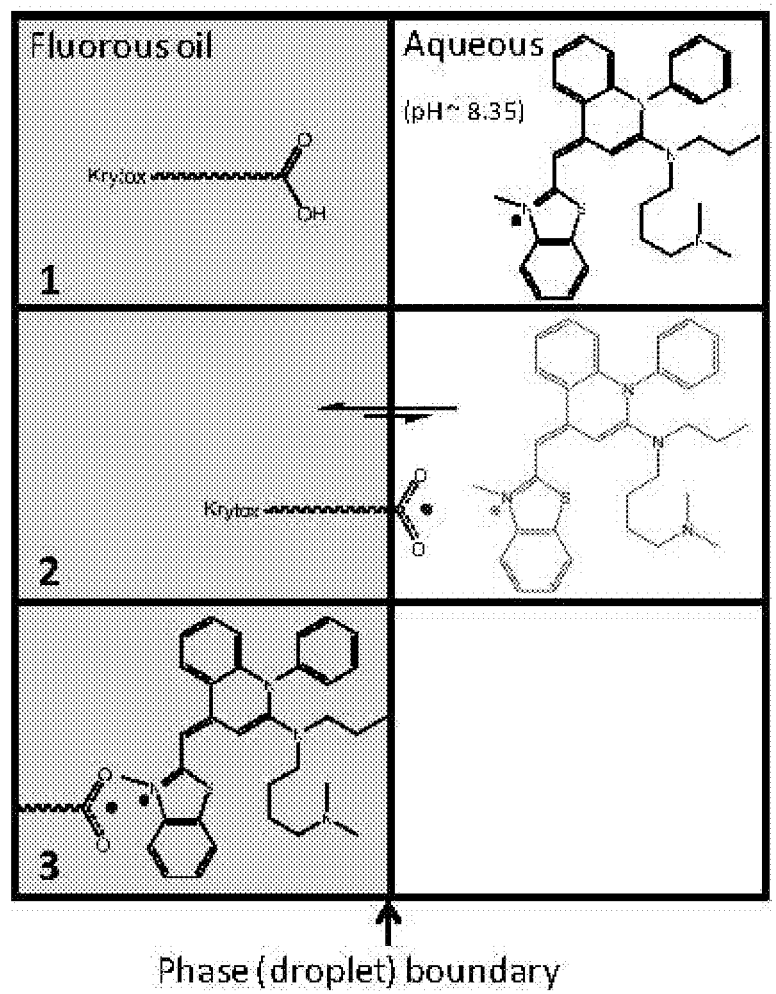

With respect to some of the high purity fluorosurfactant compositions of the present disclosure, carboxylic acid impurity is reduced or absent and the dye leaching is minimized (FIG. 2). These results may point to an alternate mechanism of dye-leaching, such that the amount of dye leaching is dependent upon the amount of the carboxylic acid impurity present in the fluorosurfactant. The new mechanism for dye leaching is schematically illustrated in FIG. 3.

In some cases, in the beginning of the ddPCR reaction, the carboxylic acid impurity is present in the continuous phase or the oil phase while, the DNA intercalating dye is present in the aqueous phase. Once the droplets are generated, the carboxylic acid compound enters the aqueous phase, where it is deprotonated. The resulting carboxylate ion then ion-pairs with the cationic intercalating dye and the neutral carboxylate/dye complex then migrates across the phase boundary into the fluorous phase. This results in a decreased relative response in observed droplet fluorescence over time, while the background fluorescence increases over time. The ion-pairing approach may be an 'active' transport mechanism, which, in some cases, may be favored over any micelle mediated transport. The ion-pair mechanism may also explain the high rate of dye leaching where significant quantity of dye is lost from the aqueous phase in just minutes, for example.

Fluorosurfactant

A surfactant may be characterized as a surface-active agent capable of reducing the surface tension of a liquid in which it is dissolved, and/or the interfacial tension with another phase. A surfactant may incorporate both a hydrophilic portion and a hydrophobic portion, which may collectively confer a dual hydrophilic-hydrophobic character on the surfactant. Fluorosurfactants, or fluorinated surfactants, are organofluorine chemical compounds that have multiple fluorine atoms. They can be either polyfluorinated or perfluorinated. In some cases, the fluorosurfactant can be non-ionic.

An aspect of the present disclosure provides a fluorous surfactant of Formula I, The surfactant of Formula I is a triblock copolymer comprising polyethylene glycol (PEG) polymer covalently linked to polyhexafluoropropylene oxide (PFPE) at both ends. In an example, the covalent linkage between the PEG block and PFPE blocks at both the ends is an amide linkage (A and B are nitrogen). In another example, the linkage between the PEG block and the two PFPE blocks is by ester bonds (A and B are oxygen). In another example, the PEG block can be linked to the PFPE blocks by an amide bond at one end and an ester bond at the other end (A is oxygen, B is nitrogen; or A is nitrogen, B is oxygen).

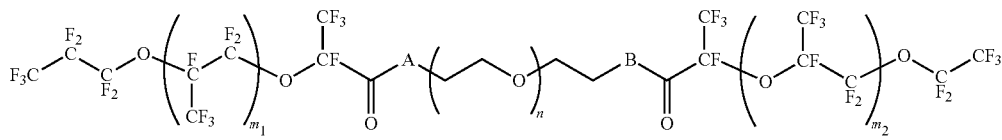

Formula I

The lengths of the PFPE chains and the PEG block may be important in determining the properties of the fluorosurfactant. In some aspects of the present disclosure both $m_1$ and $m_2$ are independently in a range of about 10-100. In some cases both m1 and m2 are independently in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. In some cases m1 is in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. In some cases m2 is in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100.

The value of 'n' in the present disclosure may be in a range of about 10-60. In some cases the value of 'n' is in the range of about 10-20, about 10-30, about 10-40, about 10-50, about 15-20, about 15-30, about 15-40, about 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, about 55-60. In some embodiments, each of $m_1$ and $m_2$ is about 35 and 'n' is about 22.

Another aspect of the current disclosure provides a high purity fluorosurfactant of Formula II. The surfactant II is a diblock copolymer of PEG and PFPE. The value of m3, which represents the length of the PFPE block, is in a range of about 10-100. In some aspects, m3 is in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. The length of the PEG unit, 'n' is in the range of about 10-60. In some cases the value of 'n' is in the range of about 10-20, about 10-30, about 10-40, about 10-50, about 15-20, about 15-30, about 15-40, about 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, or about 55-60. The end of the PEG block, —OR, can either be a hydroxyl group (i.e., —OH), an alkoxy group, or an amine—that is, R can be hydrogen, an alkyl group, or an amine.

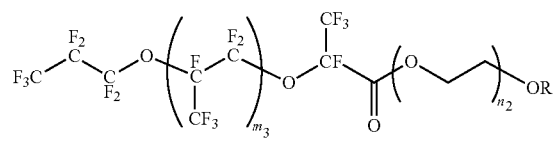

Formula II

Another aspect of the current disclosure provides a high purity fluorosurfactant of Formula III. The surfactant of Formula III is a triblock copolymer wherein two units PEG (same or different length) and one unit of PFPE are connected by a phosphate linker ($PO_4$). The length of the PFPE chain $m_4$ is in a range of about 10-100. In some cases $m_4$ is in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. The lengths of the two PEG units, $n_3$ and $n_4$ are independently in a range of about 10-60. In some cases $n_3$ and $n_4$ are independently in the range of about 10-20, about 10-30, about 10-40, about 10-50, about 15-20, about 15-30, about 15-40, about 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, or about 55-60. In some cases $n_3$ is in the range of about 10-20, about 10-30, about 10-40, about 10-50, about 15-20, about 15-30, about 15-40, 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, or about 55-60. In some cases $n_4$ is in the range of about 10-20, about 10-30, about 10-40, about 10-50, about 15-20, about 15-30, about 15-40, about 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, or about 55-60. The $CH_2$ spacer ($n_5$) can be 0, 1, 2 or 3 carbons in length.

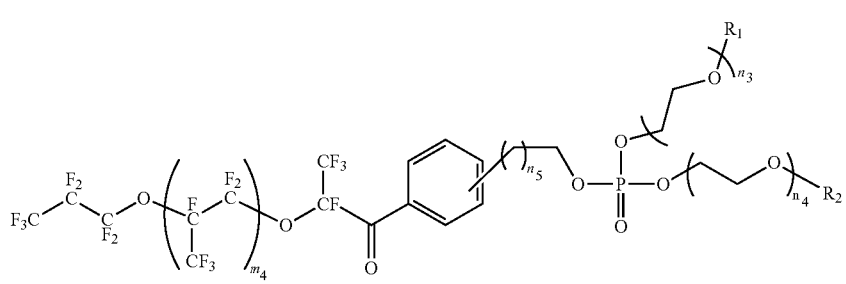

Formula III

In some cases, the fluorosurfactant can comprise a mixture of Formula I, Formula II, and/or Formula III. In certain cases, the fluorosurfactant can comprise a mixture of Formula I and Formula II. In some examples, the fluorosurfactant can comprise at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or about 99.9% (w/w) of a mixture of Formula I and Formula II. For example, the fluorosurfactant can comprise at least about 80%, about 90%, or 95% (w/w) of a mixture of Formula I and Formula II.

Further, the mixture of Formula I and Formula II can be in a ratio of greater than about 1:199, about 1:99, about 2:98, about 3:97, about 4:96, about 5:95, about 10:90, about 15:85: about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 96:4, about 97:3, about 98:2, about 99:1, or about 199:1 (w/w). For example, the mixture of Formula I and Formula II can be in a ratio of greater than about 80:20, about 90:10, or about 95:5 (w/w).

Alternatively, the mixture of Formula I and Formula II can be in a ratio of less than about 1:199, about 1:99, about 2:98, about 3:97, about 4:96, about 5:95, about 10:90, about 15:85: about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 96:4, about 97:3, about 98:2, about 99:1, or about 199:1 (w/w). For example, the mixture of Formula I and Formula II can be in a ratio of less than about 80:20, about 90:10, or about 95:5 (w/w).

In certain cases, the fluorosurfactant mixture can further comprise Formula XI:

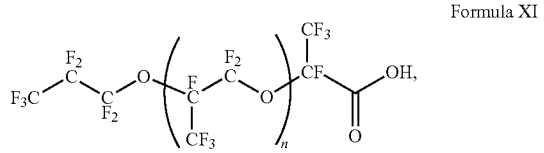

Formula XI wherein n can be about 10 to 100, about 10 to 80, about 15 to 80, about 15 to 50, or about 20 to 50.

For example, the fluorosurfactant mixture can comprise about 0.1% to 50%, about 0.1% to 20%, about 0.2% to 20%, about 0.2% to 10%, about 0.5% to 10%, about 0.5% to 5%, or about 1% to 5% (w/w) of Formula XI.

Further, the fluorosurfactant mixture can comprise about greater than about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45% or about 50% (w/w) of Formula XI. For example, the fluorosurfactant mixture can comprise about greater than about 0.1%, about 0.5%, about 1%, about 2%, or about 5% (w/w) of Formula XI.

Alternatively, the fluorosurfactant mixture can comprise about less than about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45% or about 50% (w/w) of Formula XI. For example, the fluorosurfactant mixture can comprise about less than about 1%, about 2%, about 5%, about 10%, or about 20% (w/w) of Formula XI.

In certain cases, the oil formulation can comprise less than about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45% or about 50% (w/w) of Formula XI. For example, the oil formulation can comprise about less than about 1%, about 2%, about 5%, about 10%, or about 20% (w/w) of Formula XI.

In other cases, the oil formulation can comprise greater than about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45% or about 50% (w/w) of Formula XI. For example, the oil formulation can comprise about greater than about 0.1%, about 0.5%, about 1%, about 2%, or about 5% (w/w) of Formula XI.

A surfactant may be characterized according to a Hydrophile-Lipophile Balance (HLB) value, which may be defined as the ratio of the molecular weight (MW) of the hydrophilic portion of the compound to the total MW of the compound. HLB may be controlled by varying the lengths/MWs of the hydrophobic portion (PFPE) and the hydrophilic portion (PEG) of the molecule. HLB of the fluorosurfactant may play a critical role in 'anchoring' the surfactant into the aqueous droplet. For example and without being bound to theory, decreasing the specified PEG MW may result in thermal instability due to an increased rate of exchange of surfactant at the droplet boundary, while increasing the optimized PEG MW may result in the generation of non-uniform, poly-disperse droplet populations. Furthermore, decreasing the specified PFPE molecular weight (MW) may result in loss of thermal stability due to coalescence (less dense fluorophilic brush network). In general, the longer (higher MW) the perfluoropolyether chain the greater the systems resistance to thermally induced droplet coalescence. In some embodiments, the MW of the perfluoropolyether chain is at least about 3000, at least about 4000, at least about 5000, at least about 6000, at least about 7000, at least about 8000, at least about 9000, or at least about 10000. In some other embodiments, the MW of the perfluoropolyether chain is about 3000, about 4000, about 5000, about 6000, about 7000, about 8000, about 9000, or about 10000.

In some aspects of the current disclosure, the HLB value of the fluorosurfactant is in the range of about 0-20. In some cases, the HLB values of the non-ionic surfactant ranges from about 0-10, about 0-20, about 5-10, about 5-15, about 5-20, or about 10-20. In some further aspects, the HLB value of the fluorosurfactant is about 1, about 2, about 3, about 4, about 5, about 6, about 7, about 8, about 9, about 10, about 11, about 12, about 13, about 14, about 15, about 16, about 17, about 18, about 19, or about 20.

In general, the fluorosurfactants obtained in the present disclosure are high purity fluorosurfactants and can be successfully used in ddPCR assays with intercalating dyes while avoiding dye leaching. In some cases, the fluorosurfactants can be greater than about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 85.5%, about 86%, about 86.5%, about 87%, about 87.5%, about 88%, about 88.5%, about 89%, about 89.5%, about 90%, about 90.5%, about 91.5%, about 92%, about 92.5%, about 93%, about 93.5%, about 94%, about 94.5%, about 95%, about 96.5%, about 97%, about 97.5%, about 98%, about 98.5%, about 99%, or about 99.5% weight percent (w/w) pure. In some examples, the fluorosurfactants are greater than about 90% weight percent (w/w) pure. For example, the fluorosurfactants can comprise at least 90% (w/w) of a mixture of Formula I and Formula II. In some cases the weight percent purity of the fluorosurfactant is in the range of about 90%-91% w/w, about 90%-92% w/w, about 90%-93% w/w, about 90%-94% w/w, about 90%-95% w/w, about 90%-96% w/w, about 90%-97% w/w, about 90%-98% w/w, about 90%-99% w/w, about 91%-92% w/w, about 91%-93% w/w, about 91%-94% w/w, about 91%-95% w/w, about 91%-96% w/w, about 91%-97% w/w, about 91%-98% w/w, 91%-99% w/w, about 92%-93% w/w, about 92%-94% w/w, about 92%-95% w/w, about 92%-96% w/w, about 92%-97% w/w, about 92%-98% w/w, about 92%-99% w/w, about 93%-94% w/w, about 93%-95% w/w, about 93%-96% w/w, about 93%-97% w/w, about 93%-98% w/w, about 93%-99% w/w, about 94%-95% w/w, about 94%-96% w/w, about 94%-97% w/w, about 94%-98% w/w, or about 94%-99% w/w. In some cases the fluorosurfactants are greater than about 95% (weight percent) pure. For example, the fluorosurfactants can comprise at least 95% (w/w) of a mixture of Formula I and Formula II. In some cases the weight percent purity of the fluorosurfactant is in the range of about 95%-96% w/w, about 95%-97% w/w, about 95%-98% w/w, about 95%-99% w/w, about 96%-97% w/w, about 96%-98% w/w, about 96%-99% w/w, about 97%-98% w/w, about 97%-99% w/w, or about 98%-99% w/w. In some cases, the fluorosurfactants may have weight percent purity of about 90% w/w, about 91% w/w, about 92% w/w, about 93% w/w, about 94% w/w, about 95% w/w, about 96% w/w, about 97% w/w, about 98% w/w, or about 99% w/w.

The concentration of fluorosurfactant may be important for droplet stability. In some cases, the concentration of fluorosurfactant may be in a range of 0.1-10.0 mM (millimolar). In some embodiments, the concentration of fluorosurfactant is in a range of about 0.1 mM-1.0 mM, about 0.1 mM-2.0 mM, about 0.1 mM-3.0 mM, about 0.1 mM-4.0 mM, about 0.1 mM-5.0 mM, about 0.1 mM-6.0 mM, about 0.1 mM-7.0 mM, about 0.1 mM-8.0 mM, about 0.1 mM-9.0 mM, about 0.5 mM-1.0 mM, about 0.5 mM-2.0 mM, about 0.5 mM-3.0 mM, about 0.5 mM-4.0 mM, about 0.5 mM-5.0 mM, about 0.5 mM-6.0 mM, about 0.5 mM-7.0 mM, about 0.5 mM-8.0 mM, about 0.5 mM-9.0 mM, about 0.5 mM-10.0 mM, about 1.0 mM-2.0 mM, about 1.0 mM-3.0 mM, about 1.0 mM-4.0 mM, about 1.0 mM-5.0 mM, about 1.0 mM-6.0 mM, about 1.0 mM-7.0 mM, about 1.0 mM-8.0 mM, about 1.0 mM-9.0 mM, about 1.0 mM-10.0 mM, about 1.5 mM-2.0 mM, about 1.5 mM-3.0 mM, about 1.5 mM-4.0 mM, about 1.5 mM-5.0 mM, about 1.5 mM-6.0 mM, about 1.5 mM-7.0 mM, about 1.5 mM-8.0 mM, about 1.5 mM-9.0 mM, about 1.5 mM-10.0 mM, about 2.0 mM-3.0 mM, about 2.0 mM-4.0 mM, about 2.0 mM-5.0 mM, about 2.0 mM-6.0 mM, about 2.0 mM-7.0 mM, about 2.0 mM-8.0 mM, about 2.0 mM-9.0 mM, about 2.0 mM-10.0 mM, about 2.5 mM-3.0 mM, about 2.5 mM-4.0 mM, about 2.5 mM-5.0 mM, about 2.5 mM-6.0 mM, about 2.5 mM-7.0 mM, about 2.5 mM-8.0 mM, about 2.5 mM-9.0 mM, about 2.5 mM-10.0 mM, about 3.0 mM-4.0 mM, about 3.0 mM-5.0 mM, about 3.0 mM-6.0 mM, about 3.0 mM-7.0 mM, about 3.0 mM-8.0 mM, about 3.0 mM-9.0 mM, about 3.0 mM-10.0 mM, about 3.5 mM-4.0 mM, about 3.5 mM-5.0 mM, about 3.5 mM-6.0 mM, about 3.5 mM-7.0 mM, about 3.5 mM-8.0 mM, about 3.5 mM-9.0 mM, about 3.5 mM-10.0 mM, about 4.0 mM-5.0 mM, about 4.0 mM-6.0 mM, about 4.0 mM-7.0 mM, about 4.0 mM-8.0 mM, about 4.0 mM-9.0 mM, about 4.0 mM-10.0 mM, about 4.5 mM-5.0 mM, about 4.5 mM-6.0 mM, about 4.5 mM-7.0 mM, about 4.5 mM-8.0 mM, about 4.5 mM-9.0 mM, about 4.5 mM-10.0 mM, about 5.0 mM-6.0 mM, about 5.0 mM-7.0 mM, about 5.0 mM-8.0 mM, about 5.0 mM-9.0 mM, about 5.0 mM-10.0 mM, about 5.5 mM-6.0 mM, about 5.5 mM-7.0 mM, about 5.5 mM-8.0 mM, about 5.5 mM-9.0 mM, about 5.5 mM-10.0 mM, about 6.0 mM-7.0 mM, about 6.0 mM-8.0 mM, about 6.0 mM-9.0 mM, about 6.0 mM-10.0 mM, about 6.5 mM-7.0 mM, about 6.5 mM-8.0 mM, about 6.5 mM-9.0 mM, about 6.5 mM-10.0 mM, about 7.0 mM-8.0 mM, about 7.0 mM-9.0 mM, about 7.0 mM-10.0 mM, about 7.5 mM-8.0 mM, about 7.5 mM-9.0 mM, about 7.5 mM-10.0 mM, about 8.0 mM-9.0 mM, about 8.0 mM-10.0 mM, about 8.5 mM-9.0 mM, about 8.5 mM-10.0 mM, about 9.0 mM-10.0 mM, or about 9.5 mM-10.0 mM. In some other embodiments, the concentration of fluorosurfactant is about 0.5 mM, about 1.0 mM, about 1.5 mM, about 2.0 mM, about 2.5 mM, about 3.0 mM, about 3.5 mM, about 4.0 mM, about 4.5 mM, about, 5.0 mM, about 5.5 mM, about 6.0 mM, about 6.5 mM, about 7.0 mM, about 7.5 mM, about 8.0 mM, about 8.5 mM, about 9.0 mM, or about 9.5 mM.

Oil Phase

The oil phase or the continuous phase used in this disclosure is any liquid compound or mixture of liquid compounds that is immiscible with water. The oil used may be or include at least one of silicone oil, mineral oil, hydrocarbon oil, fluorocarbon oil, vegetable oil, or a combination thereof, among others. Any other suitable components may also be present in the oil phase, such as at least one surfactant, reagent, other additive, preservative, particles, or any combination thereof.

In some cases, the oil is fluorinated oil. Fluorinated oil can be any fluorinated organic compound. In some cases, the fluorinated oil is perfluorocarbon, such as perfluorooctane or perfluorohexane. In some cases, the fluorine-containing compound is a partially fluorinated hydrocarbon, such as 1,1,1-trifluorooctane or 1,1,1,2,2-petantafluorodecane. The fluorinated organics can be linear, cyclic or heterocyclic. In addition to carbon and fluorine, the fluorinated organic compound can further contain hydrogen, oxygen, nitrogen, sulfur, chlorine, bromine atoms.

In some cases, the fluorinated oil is a perfluoroalkyl ether like methyl nonafluoroisobutyl ether sold as NOVEC™ HFE-7100 Engineered Fluid. In some cases, the fluorine-containing compound is 3-ethoxy-1,1,1,2,3,4,4,5,5,6,6,6-dodecafluoro-2-trifluoromethyl-hexane, sold as NOVEC™ HFE-7500 Engineered Fluid. In some cases, the fluorine-containing compound is 3-ethoxy-1,1,1,2,3,4,4,5,5,6,6,6-dodecafluoro-2-trifluoromethyl-hexane, sold as NOVEC™ HFE-7500 Engineered Fluid. In some cases, the fluorine-containing compound can be 1,1,1,2,2,3,4,5,5,5-decafluoro-3-methoxy-4-(trifluoromethyl)pentane, sold as NOVEC™ HFE-7300 Engineered Fluid.

In the methods of the present disclosure, the fluorosurfactants reside mainly in the oil phase. In some cases at least about 90%, about 91%, about 92%, about 93%, about 94%, about 95%, about 96%, about 97%, about 98%, or about 99% of the fluorosurfactant resides in the oil phase.

Aqueous Phase

The aqueous phase can be any liquid miscible with water. That is, aqueous phase can be any liquid that when mixed with water at room temperature, forms a stable single phase solution. In some embodiments the aqueous phase can comprise one or more physiologically acceptable reagents and/or solvents etc. Some non-limiting examples of aqueous phase include water, DMF, DMSO, methanol or ethanol.

In some cases, the aqueous phase can be a buffer solution. The buffered solution can comprise of TRIS and KCl. In some cases, the concentration of Tris is about, more than about, or less than about 1 mM, 5 mM, 10 mM, 15 mM, 20 mM, 30 mM, 50 mM, 80 mM, 160 mM, or 200 mM. In some cases, the concentration of potassium chloride can be about, more than about, or less than about 10 mM, about 20 mM, about 30 mM, about 40 mM, about 50 mM, about 60 mM, about 80 mM, about 100 mM, about 200 mM. The buffered solution can comprise about 160 mM Tris and about 40 mM KCl. In some cases, magnesium chloride ($MgCl_2$) is added to an amplification reaction at a concentration of about, more than about, or less than about 1.0 mM, about 2.0 mM, about 3.0 mM, about 4.0 mM, or about 5.0 mM.

In some cases the pH of the buffered aqueous phase is in the range of about 7.0-10.0. In some cases the pH of the aqueous phase is in the range of about 7.5-10.0, about 8.0-10.0, about 8.5-10.0, about 9.0-10.0, about 9.5-10.0, about 7.0-9.5, about 7.5-9.5, about 8.0-9.5, about 8.5-9.5, about 9.0-9.5, about 7.0-9.0, about 7.5-9.0, about 8.0-9.0, about 8.5-9.0, about 7.0-8.5, about 7.5-8.5, about 8-8.5, about 7.0-8.0, or about 7.5-8.0. In some cases the pH of the aqueous solution is about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, or about 10.

Non-Ionic Non-Fluorosurfactant

The aqueous phase of the present disclosure further comprises a non-ionic non-fluorosurfactant. Surfactant is a surface active substance capable of reducing the surface tension of a liquid in which it is present. A surfactant, which also or alternatively may be described as a detergent and/or wetting agent, may incorporate both a hydrophilic portion and a hydrophobic portion, which may collectively confer a dual hydrophilic-hydrophobic character on the surfactant. A surfactant may, in some cases, be characterized according to its hydrophilicity relative to its hydrophobicity. In some embodiments, the non-ionic non-fluorosurfactant is a polyalkylene oxide block copolymer surfactant. Particularly useful are block copolymers of polypropylene glycol (H—(O—$CH(CH_3)$—$CH_2)_n$—OH, PPG) and polyethylene glycol (H—(O—$CH_2$—$CH_2)_n$—OH, PEG) having the general formula [PPGn-PEGm].

The non-ionic non-fluorosurfactant could be a di, tri, tetra, penta or even higher block polymer of PEG and PPG. In some cases the non-ionic non-fluorosurfactant is an alternating copolymer with regular alternating PEG and PPG units of general formula (PEG-PPG)x, wherein x is in the range of about 10-100. In some cases, x is in the range of about 10-20, about 10-30, about 10-40, about 10-50, about 10-60, about 10-70, about 10-80, about 10-90, about 20-30, about 20-40, about 20-50, about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. In some cases the non-ionic non-fluorosurfactant is a random copolymer of PEG and PPG with the monomeric PEG and PPG blocks attached in a random sequence.

In some cases the molecular weight of PEG and PPG block copolymer is in the range of about 4,000 dalton ("Da")-25,000 Da. In some cases the molecular weight of the non-ionic non-fluorosurfactant is in the range of about 10,000 Da-25000 Da, about 15,000 Da-25,000 Da, about 20,000 Da-25,000 Da, about 4,000 Da-20,000 Da, about 10,000 Da-20000 Da, about 15,000 Da-20,000 Da, about 4,000 Da-15,000 Da, about 10,000 Da-15,000 Da, or about 4,000 Da-10,000 Da. In some cases the molecular weight of the non-ionic non-fluorosurfactant is about 4,000 Da, 4,500 Da, about 5,000 Da, about 5,500 Da, about 6,000 Da, about 6,500 Da, about 7,000 Da, about 7,500 Da, about 8,000 Da, about 8,500 Da, about 9,000 Da, about 9,500 Da, about 10,000 Da, about 10,500 Da, about 11,000 Da, about 11,500 Da, about 12,000 Da, about 12,500 Da, about 13,000 Da, about 13,500 Da, about 14,000 Da, about 14,500 Da, about 15,000 Da, about 15,500 Da, about 16,000 Da, about 16,500 Da, about 17,000 Da, about 17,500 Da, about 18,000 Da, about 18,500 Da, about 19,000 Da, about 19,500 Da, about 20,000 Da, about 20,500 Da, about 21,000 Da, about 21,500 Da, about 22,000 Da, about 22,500 Da, about 23,000 Da, about 23,500 Da, about 24,000 Da, about 24,500 Da or about 25,000 Da.

In some cases, the non-ionic non-fluorosurfactant is a triblock copolymer of polypropylene oxide and polyethylene oxide (Scheme 3, Formula VI, see below) sold under the trade names Pluronic® (registered trademark of BASF Corporation, also known under non-proprietary name "poloxamers"). These copolymers consist of a central hydrophobic chain of PPG flanked by two hydrophilic chains of PEG (PEG-PPG-PEG). The block copolymers with varying length of the individual PEG and PPG units are characterized by different hydrophilic-lipophilic balance (HLB). In some embodiments, the Pluronic® surfactant is Pluronic® F-38, Pluronic® F-68, Pluronic® F-77, Pluronic® F-87, Pluronic® F-88, Pluronic®F-98, Pluronic® F-108 or Pluronic® F-127 (a=101, b=56).

In further embodiments of the disclosure the non-ionic non-fluorous surfactant is Nonidet® P40 (registered trade mark of Shell Chemical Co.). The general structure of Nonidet® comprises of a hydrophilic polyethylene chain and an aromatic hydrocarbon lypophilic group (Scheme 3, Formula VII, see below). In some cases the non-ionic non-fluorous surfactant is Nonidet® P40.

In further embodiments of the disclosure the non-ionic non-fluorous surfactant can be other polyethylene glycol derivatives including Triton® X100 (registered trademark of Union Carbide Corp.). The general structure of Triton® comprises of a hydrophilic polyethylene chain and an aromatic hydrocarbon lypophilic group (Scheme 3, Formula VIII, see below). In some cases the non-ionic non-fluorous surfactant is Triton® X-15 (x=1.5 avg), Triton® X-35 (x=3 avg), Triton® X-45 (x=4.5 avg), Triton® X-100 (x=9.5 avg), Triton® X-102 (x=12 avg), Triton® X-114 (x=7.5 avg), Triton® X-165 (x=16 avg), Triton® X-305 (x=30 avg), Triton® X-405 (x=35 avg), or Triton® X-705 (x=1.5 avg).

In further embodiments of the disclosure the non-ionic non-fluorous surfactant is a polyoxyethylene derivative of sorbitan monolaurate (Scheme 3, Formula IX, see below), commercially available as Tween® (registered trademark of Uniquema Americas LLC). In some cases, the non-ionic non-fluorous surfactant is Tween® 20 (R=$CH_2(CH_2)_9CH_3$)), Tween® 40 (R=$CH_2(CH_2)_{13}CH_3$), Tween® 60 (R=$CH_2(CH_2)_{15}CH_3$) or Tween®-80 (R=$(CH_2)_7CH=CH(CH_2)_8$.

Scheme 3

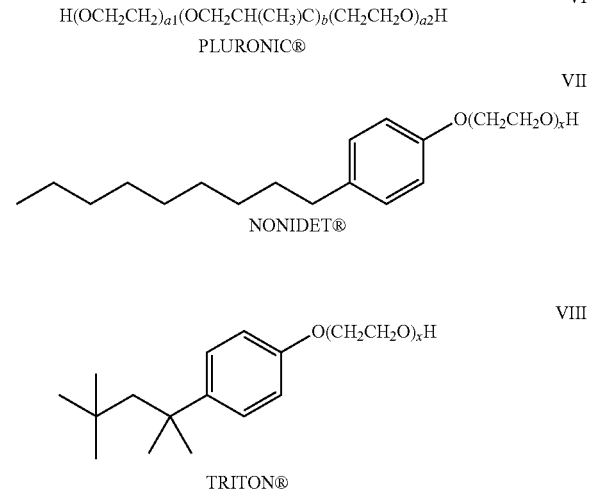

-continued

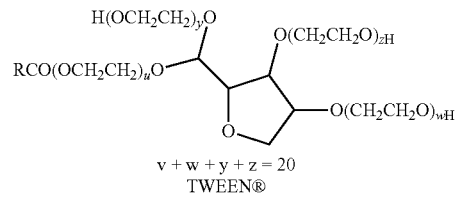

IX v + w + y + z = 20
TWEEN®

The concentration of non-ionic non-fluorosurfactant may be in a range of about 0.1-5.0% weight percent. In some embodiments the concentration of the non-ionic non-fluorosurfactant is less than about 1.5% weight by weight ("w/w"). In some cases, the concentration of Pluronic® is less than about 1.4% w/w, about 1.3% w/w, about 1.2% w/w, about 1.1% w/w, about 1.0% w/w, about 0.9% w/w, about 0.8% w/w, about 0.7% w/w, about 0.6% w/w, about 0.5% w/w, about 0.4% w/w, about 0.3% w/w, about 0.2% w/w or about 0.1% w/w. In some embodiments the Pluronic®F-98 concentration is in the range of about 0.50% w/w-1.5% w/w. In some embodiments the Pluronic®F-98 concentration is in the range of about 0.50% w/w-0.60% w/w, about 0.50% w/w-0.65% w/w, about 0.50% w/w-0.70% w/w, about 0.55% w/w-0.60% w/w, about 0.55% w/w-0.65% w/w, about 0.55% w/w-0.70% w/w, about 0.55% w/w-0.75% w/w, about 0.60% w/w-0.65% w/w, about 0.60% w/w-0.70% w/w, about 0.60% w/w-0.75% w/w, about 0.65% w/w-0.70% w/w, about 0.65% w/w-0.75% w/w, or about 0.70% w/w-0.75% w/w. In some further embodiments the concentration of the non-ionic non-fluorous surfactant can be adjusted to optimize the droplet stability and droplet size without inhibiting the PCR assay.

In some embodiments, the concentration of fluorosurfactant is in a range of about 1.0-6.0 mM and the concentration of non-ionic non-fluorosurfactant is in a range of about 0.1%-3.0% weight percent. In a further embodiment, the fluorosurfactant has a structure of Formula I and a concentration of about 2.5 mM, and the non-ionic non-fluorosurfactant is Pluronic® F-98 and has a concentration of about 0.5% w/w-1.5% w/w. In some cases, the fluorosurfactant has a structure of Formula I and a concentration of about 2.5 mM, and the non-ionic non-fluorosurfactant is Pluronic® F-98 and has a concentration of about 0.50% w/w-0.60% w/w, about 0.50% w/w-0.65% w/w, about 0.50% w/w-0.70% w/w, about 0.55% w/w-0.60% w/w, about 0.55% w/w-0.65% w/w, about 0.55% w/w-0.70% w/w, about 0.55% w/w-0.75% w/w, about 0.60% w/w-0.65% w/w, about 0.60% w/w-0.70% w/w, about 0.60% w/w-0.75% w/w, about 0.65% w/w-0.70% w/w, about 0.65% w/w-0.75% w/w, or about 0.70% w/w-0.75% w/w.

In the methods of the present invention, the non-ionic non-fluorous surfactants reside essentially in the aqueous phase. In some cases at least about 90%, about 91%, about 92%, about 93%, about 94%, about 95%, about 96%, about 97%, about 98%, or about 99% of the non-ionic non-fluorous surfactant resides in the aqueous phase of the aqueous droplets.

Intercalating Dye

Intercalating dyes are generally aromatic cations with planar structures that insert between stacked base pairs in the DNA duplex, an arrangement that provides an environmentally dependent fluorescence enhancement for dye molecules and creates a large increase in the fluorescence signal relative to the free dye in solution. The signal enhancement provides a proportional response, allowing direct quantitative DNA measurements. Preferred intercalating dyes in the present disclosure include fluorescent dyes. The dye can be a cyanine or a non-cyanine intercalating die. In some cases, the intercalating dye is a cyanine dye. In some cases the cyanine dye can be Thiazole Orange, SYBR® (e.g. Sybr Green I, Syber Green II, Sybr Gold, SYBR DX), Oil Green, CyQuant GR, SYTOX Green, SYTO9, SYTO10, SYTO17, SYBR14, Oxazile Yellow, Thiazone Orange, SYTO, TOTO, YOYO, BOBO, and POPO. In some cases the dye is a non-cyanine dye. In some cases the non cyanine dye is pentacene, anthracene, naphthalene, ferrocene, methyl viologen, tri-morpholino ammonium, propidium (e.g. propidium iodide) or another aromatic or heteroaromatic derivative. In some cases, the intercalating dye can be EvaGreen®.

Other Additives

In some embodiments, an amplification reaction can also comprise one or more additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). The one or more additives can include, e.g., 2-pyrrolidone, acetamide, N-methylpyrrolidone (NMP), B-hydroxyethylpyrrolidone (HEP), propionamide, NN-dimethylacetamide (DMA), N-methylformamide (MMP), NN-dimethylformamide (DMF), formamide, N-methylacetamide (MMA), dimethyl sulfoxide (DMSO), polyethylene glycol, betaine, tetramethylammonium chloride (TMAC), 7-deaza-2'-deoxyguanosine, bovine serum albumin (BSA), T4 gene 32 protein, or glycerol.

Devices and Systems

In another aspect, the present disclosure provides a droplet generation system, comprising: (a) a first channel in fluid communication with a carrier fluid source, wherein the carrier fluid source comprises an oil and a fluorosurfactant, and wherein the fluorosurfactant is selected from Formula I, II and/or III; (b) a second channel in fluid communication with a sample source, wherein the sample source comprises a target nucleic acid, a non-ionic surfactant and an intercalating dye; (c) a droplet channel; and (d) a droplet source; wherein the first channel meets the second channel at an intersection; the intersection receives a sample from the sample source and a carrier fluid from the carrier fluid source and generates emulsified droplets; and the emulsified droplets flow along the droplet channel to the droplet source.

Figure 7:
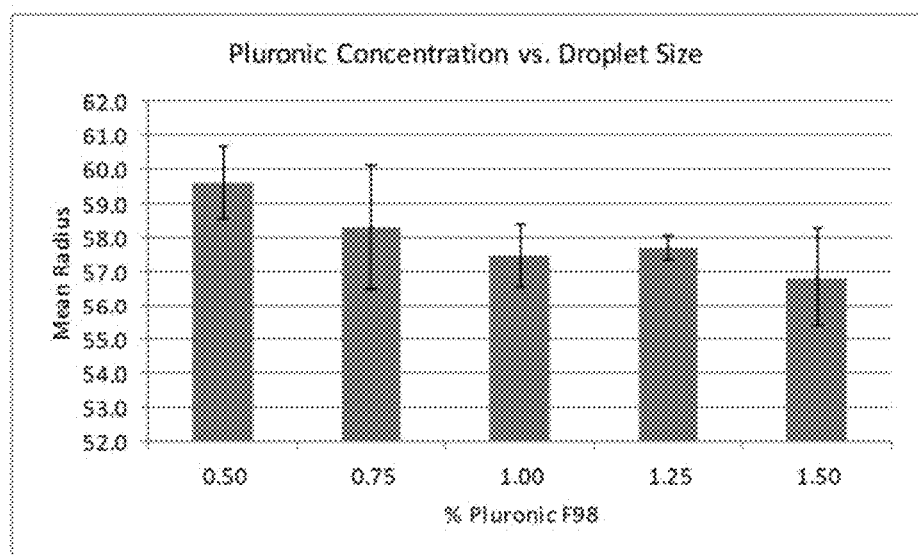
FIG. 7 schematically illustrates a droplet generator, in accordance with an embodiment of the present disclosure.

FIG. 7 shows a schematic representation of a droplet generation system 100 comprising a sample source 105 in fluid communication with a sample channel 110, and a carrier fluid source 115 in fluid communication with a carrier fluid channel. The sample channel 110 and the carrier fluid channel 115 meet at an intersection or a droplet generation point 125. During the operation the carrier fluid comprising oil and a fluorosurfactant from the carrier fluid source 115 is directed through the carrier fluid channels 120 to the intersection 125. The sample from the sample source 105 comprising a target nucleic acid, a non-ionic surfactant and an intercalating dye is also directed to the intersection through the sample channels, wherein a sample partition generate a droplet comprising an aqueous phase in an oil phase. A droplet thus formed flows in a droplet channel 130 from the intersection 125 to a droplet source 135 for holding the droplets.

In some situations, the system includes a detection assembly in fluid communication with the fluid flow path. The detection assembly may be situated along at least a portion of the detection channel between the intersection and the collection source. The detection assembly can be configured to detect signals from droplets in the fluid flow path, such as upon flowing through the detection channel. The detection assembly can include an optical sensor or other electronic detector that is sensitive to a select frequency of light. The sensor can be adapted to detect fluorescent emission, for example. In some cases, the detection assembly can include an excitation source, such as a light source that is adapted to induce fluorescence in the fluid. One or more optical elements (e.g., mirrors, lenses) can be provided to direct light emitted from the fluid to the detection assembly, and/or to direct light from a light source to the fluid.

In some embodiments, the system includes a pressure source for facilitating the flow of droplets from the intersection to the collection source. The pressure source can be a source of positive pressure operatively coupled to the carrier fluid and/or sample source, or a source of negative pressure (i.e., vacuum) operatively coupled to the fluid flow path, such as by way of the collection source. The source of negative pressure can be a pumping system.

The droplet generation system 100 can include a droplet detector. In some examples, the droplet detector is fluidically isolated from the droplet channel 130, but upon formation, droplets are transferred to the droplet detector for droplet detection and sample quantification. In other examples, the droplet detector is in fluid communication with the droplet channel 130. For instance, the droplet detector can be situated along the droplet channel 130. Various features, components and uses of the droplet detector may be as described in, for example, U.S. Patent Publication No. 2010/0173394 to Colston et al. ("Droplet-based assay system"), which is entirely incorporated herein by reference.

Method of Nucleic Acid Detection

Another aspect of the disclosure provides a method of detecting a nucleic acid. The method comprises: (a) providing an oil composition comprising a fluorosurfactant, wherein the fluorosurfactant is selected from the group consisting of Formula I, II and III; (b) providing an aqueous composition comprising a target nucleic acid, a non-ionic surfactant and an intercalating dye; (c) contacting the oil composition of (a) with the aqueous composition of (b), thereby generating a plurality of droplets suspended in a continuous phase; (d) thermally cycling the plurality of droplets to amplify the target nucleic acid; and (e) detecting the target nucleic acid.

The plurality of droplets generated by this method may be aqueous droplets encapsulated by an oil phase. The encapsulation may provide enhanced stability of the droplets and/or dye concentration inside the droplets.

In some embodiments, less than about 1%, about 2%, about 3%, about 4%, about 5%, about 6%, about 7%, about 8%, about 9%, about 10%, about 15%, about 20%, about 25%, about 30%, about 35%, about 40%, about 45%, or about 50% of total intercalating dyes are detected outside the aqueous phase of the aqueous droplets. In some cases, the detection can be after about 5 thermal cycles, about 10 thermal cycles, about 15 thermal cycles, about 20 thermal cycles, about 30 thermal cycles, about 40 thermal cycles, about 50 thermal cycles, about 60 thermal cycles, about 70 thermal cycles, about 80 thermal cycles, about 90 thermal cycles, about 100 thermal cycles, about 120 thermal cycles, about 150 thermal cycles, about 200 thermal cycles, about 300 thermal cycles, about 400 thermal cycles, about 500 thermal cycles or even more thermal cycles.

In some embodiments, less than about 1%, about 2%, about 3%, about 4%, about 5%, about 6%, about 7%, about 8%, about 9%, about 10%, about 15%, about 20%, about 25%, about 30%, about 35%, about 40%, about 45%, or about 50% of a specific intercalating dye (e.g. EvaGreen®, SYBR Green®) can be detected outside the aqueous phase of the aqueous droplets. In some cases, the detection can be after about 5 thermal cycles, about 10 thermal cycles, about 15 thermal cycles, about 20 thermal cycles, about 30 thermal cycles, about 40 thermal cycles, about 50 thermal cycles, about 60 thermal cycles, about 70 thermal cycles, about 80 thermal cycles, about 90 thermal cycles, about 100 thermal cycles, about 120 thermal cycles, about 150 thermal cycles, about 200 thermal cycles, about 300 thermal cycles, about 400 thermal cycles, about 500 thermal cycles or even more thermal cycles.

Individually, each of the plurality of droplets may comprise 0 target nucleic acids, 1 target nucleic acid, 2 target nucleic acids, 3 target nucleic acids, 4 target nucleic acids, 5 target nucleic acids, 6 target nucleic acids, 7 target nucleic acids, 8 target nucleic acids, 9 target nucleic acids, 10 target nucleic acids, 11 target nucleic acids, 12 target nucleic acids, 13 target nucleic acids, 14 target nucleic acids, or 15 target nucleic acids prior to thermal cycling. After thermal cycling, each of plurality of droplet can comprise about $15 \times 10^{40}$ target nucleic acids, about $14 \times 10^{40}$ target nucleic acids, about $13 \times 10^{40}$ target nucleic acids, about $12 \times 10^{40}$ target nucleic acids, about $11 \times 10^{40}$ target nucleic acids, about $10 \times 10^{40}$ target nucleic acids, about $9 \times 10^{40}$ target nucleic acids, about $8 \times 10^{40}$ target nucleic acids, about $7 \times 10^{40}$ target nucleic acids, about $6 \times 10^{40}$ target nucleic acids, about $5 \times 10^{40}$ target nucleic acids, about $4 \times 10^{40}$ target nucleic acids, about $3 \times 10^{40}$ target nucleic acids, about $2 \times 10^{40}$ target nucleic acids, about $1 \times 10^{40}$ target nucleic acid or 0 target nucleic acids.

The average number of target nucleic acid copies present per droplet prior to thermal cyclic can be in the range of about 0.00005-5 target nucleic acid per droplet. In some cases the average number of target nucleic acids present per droplet prior to thermal cycling is about 0.0001-5 target nucleic acids per droplet, about 0.001-5 target nucleic acids per droplet, about 0.01-5 target nucleic acids per droplet, about 0.1-5 target nucleic acids per droplet or about 1-5 target nucleic acids per droplet. Furthermore, after thermal cycling the average number of target nucleic per droplet could be less than about $5.5 \times 10^6$ target nucleic acids per droplet, about $5.5 \times 10^7$ target nucleic acids per droplet, about $5.5 \times 10^8$ target nucleic acids per droplet, about $5.5 \times 10^9$ target nucleic acids per droplet, $5.5 \times 10^{11}$ target nucleic acids per droplet, or about $5.5 \times 10^{12}$ target nucleic acids per droplet, per droplet. In some embodiment, the detecting comprises measuring fluorescence from the intercalating dyes.

PCR nucleic acid amplification may rely on thermal cycling (i.e., alternating cycles of heating and cooling) to achieve successive rounds of replication. In an example, during DNA melting, two strands in a DNA double helix are separated (e.g., at a high temperature). Each strand can then be used (e.g., at a lower temperature) as the template in DNA synthesis by the DNA polymerase to selectively amplify the target DNA.

PCR can be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR can be performed with a thermostable polymerase. Some non limiting examples of thermostable DNA polymerase include Taq DNA polymerase, Pfu DNA polymerase, Vent polymerase, S-Tbr polymerase, Tth polymerase, or a combination thereof.

Detection of PCR products can be accomplished using fluorescence techniques. DNA-intercalating dyes exhibit an increased fluorescence upon binding to DNA and can provide a quantitative readout of the amount of DNA present in a reaction volume. As this amount of DNA increases over the course of a reaction, the fluorescence intensity increases. Fluorescence detection can be achieved using a variety of detector devices equipped with a module to generate excitation light that can be absorbed by a fluorescent dye, as well as a module to detect light emitted by the fluorescent dye. In some embodiments, droplets can be detected in bulk. For example, samples can be allocated in tubes that are placed in a detector that measures bulk fluorescence from tubes. In some embodiments, one or more droplets can be partitioned into one or more wells of a plate, such as a 96-well plate, and fluorescence of individual wells can be detected using a fluorescence plate reader.

EXAMPLES

Example 1

FIG. 1-FIG. 2 shows that the dye leaching response is dependent on the concentration of the carboxylic acid XI.

1 ml aliquots of an aqueous solution of SYBR Green (final concentration=0.5×) were overlaid on 1 ml solutions of HFE-7500 containing known concentrations of carboxylic acid XI (0.01 mM-0.10 mM). At 1 minute intervals a 1 µl aliquot of the aqueous SYBR Green solution was taken for interrogation by UV-Vis spectroscopy at 528 nm using a NanoDrop UV/Vis spectrophotometer (Thermo Scientific). The UV-Vis response was normalized then plotted as a function of time (minutes) for each concentration. FIG. 1 clearly indicates that the rate of leaching of SYBR Green from the aqueous phase into the fluorous phase is proportional to the concentration of carboxylic acid XI present in the fluorinated oil (HFE-7500). The rate of dye leaching increases as the concentration of carboxylic acid XI increases.

A second experiment was performed in an analogous fashion to that described above. In this case, the first solution contained carboxylic acid XI at a concentration of 2.5 mM in HFE-7500, the second solution contained the fluorosurfactant XII at a concentration of 2.5 mM in HFE-7500, while the third solution was neat HFE-7500 (used as a control). FIG. 2 clearly illustrates retention of SYBR Green dye within the aqueous phase for neat HFE-7500 and the solution containing 2.5 mM of fluorosurfactant XII. The relative UV-Vis responses remained constant over time in both cases, this was in stark contrast to the HFE-7500 solution containing 2.5 mM carboxylic acid XI which significantly decreased over time.

Example 2

Figure 4:
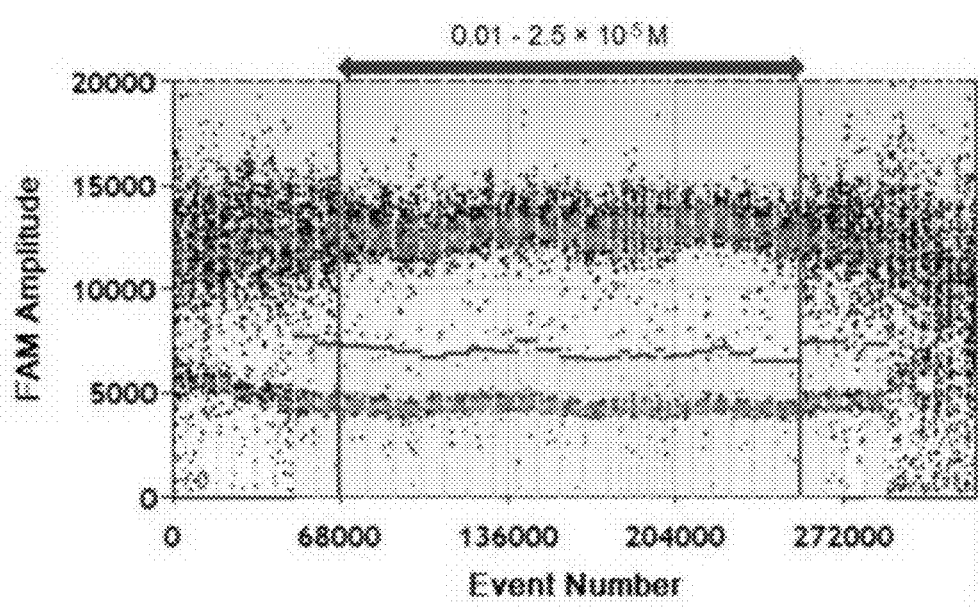

FIG. 4 shows that Bis-Krytox 157FSH-PEG1000 (XII) provides stabilization of aqueous-in-fluorous oil droplets over a large range of concentrations, and in conjunction with the aqueous surfactant (Pluronic®-F98) the optimum concentration is 2.5 mM.

In this experiment the concentration range of fluorosurfactant XII required for adequate droplet stabilization was studied through functional testing. Various solutions of fluorosurfactant XII, ranging in concentration from $1.0 \times 10^{-5}$-0.1 M, were prepared in HFE-7500. Assay droplets containing 1 cpd. *S. Aureus* template, primers, DNA polymerase, and 1× EvaGreen® in a buffered aqueous ddPCR master mix were generated from each of the fluorosurfactant solutions (4 wells, or reactions, per concentration) by a standard method using a QX100™ Droplet Generator (Bio-Rad). Droplets were transferred to a 96-well PCR plate then cycled on a C1000 Touch™ Thermal Cycler (Bio-Rad) using a standard ddPCR thermal cycling protocol. Each well of droplets was then interrogated using a modified QX100™ Droplet Reader to count positive (high fluorescence intensity) and negative (low fluorescence intensity) droplets. FIG. 4 indicates a wide working concentration range for fluorosurfactant XII of $1.0 \times 10^{-2}$-$2.5 \times 10^{-5}$ M in HFE-7500. At concentrations below or above these values droplet integrity suffers as evidenced by the large increase in 'rain' (off-amplitude signals) and merging of the positive and negative droplet populations.

Example 3

Figure 5:
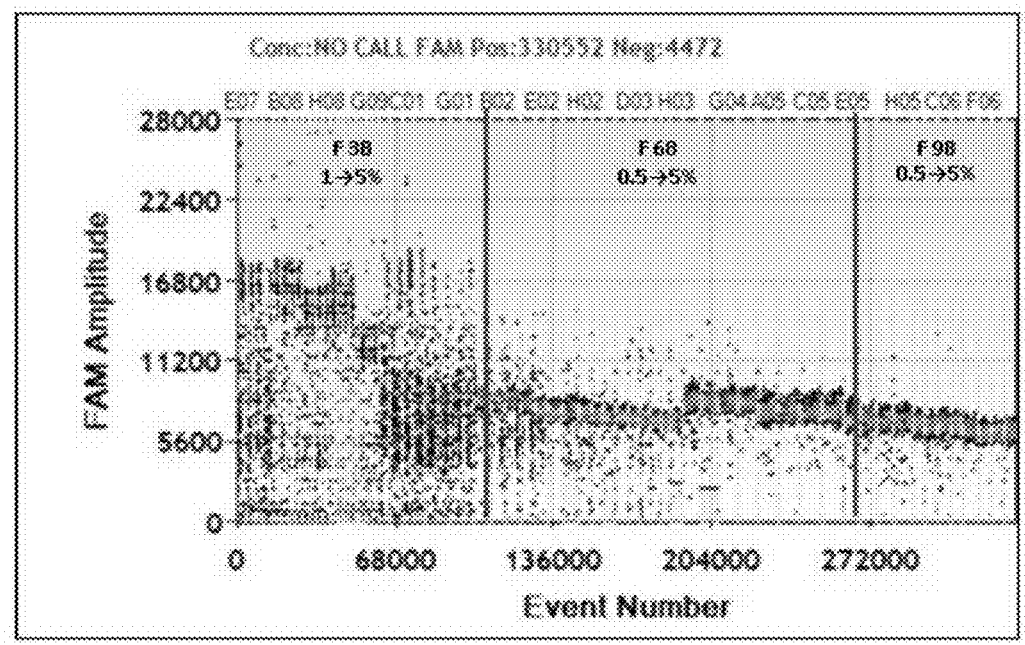
Figure 6:
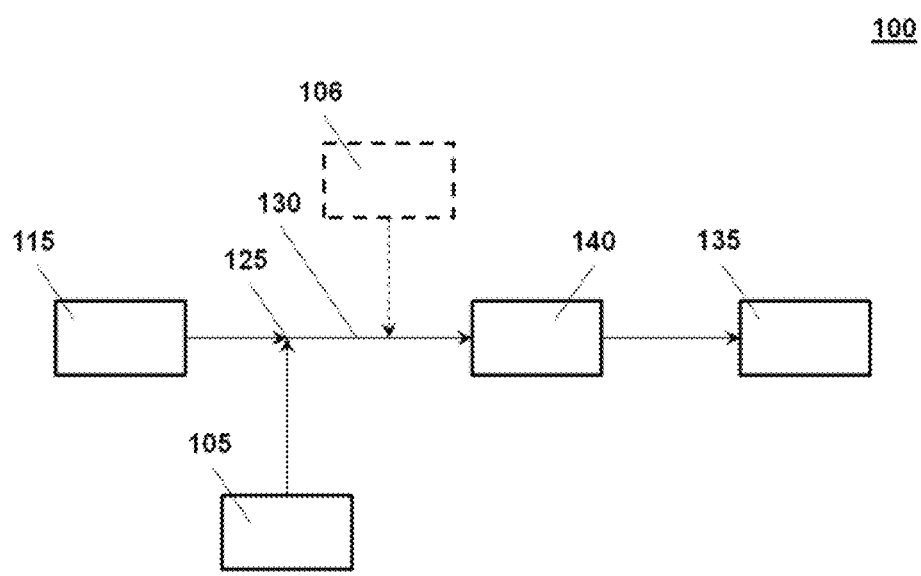
FIG. 6 is a graphical representation of the effect of Pluronic® F-98 concentration on droplet size, in accordance with an embodiment of the present disclosure.

FIG. 5 shows the effect of Pluronic® type and concentration on droplet stability In this experiment the droplet stabilizing effect of Pluronic® was studied by adding various types of Pluronic to the aqueous phase of the droplets at a range of concentrations. The types of Pluronic® studied included F-38, F-68, and F-98, typical concentrations were 0.5-5.0% w/w. Buffered aqueous solutions containing 1× EvaGreen®, primers, and the specified concentration and type of Pluronic® were prepared. Droplets containing the various aqueous solutions were generated using fluorosurfactant XII at a concentration of 2.5 mM in HFE-7500 (4 wells per Pluronic® type and concentration) by a standard method using a QX100™ Droplet Generator (Bio-Rad). Droplets were transferred to a 96-well PCR plate then cycled on a C1000 Touch™ Thermal Cycler (Bio-Rad) using a standard ddPCR thermal cycling protocol. Each well of droplets was then interrogated using a modified QX100™ Droplet Reader to assess the droplet integrity using various droplet quality metrics. FIG. 5 suggests that as the MW of the Pluronic® increases (while maintaining a constant HLB), from Pluronic® F-38 to F-98 the stability of the droplets to thermal degradation/coalescence also increases.

Example 4

FIG. 7 shows the effect of Pluronic®-F98 concentration on droplet size.

This experiment involved the titration of Pluronic® F-98 in an aqueous master mix from 0.50-1.50% w/w to determine the effect of Pluronic® concentration on the measured droplet size following droplet generation. Buffered aqueous solutions containing 1× EvaGreen®, primers, and the specified concentration of Pluronic® were prepared. Droplets containing the various aqueous solutions were generated using fluorosurfactant XII at a concentration of 2.5 mM in HFE-7500 (8 wells per Pluronic concentration) by a standard method using a QX100™ Droplet Generator (Bio-Rad). The droplets generated were removed from the outlet well, then sized by microscopy on a glass microscope slide. FIG. 7 clearly indicates that as the concentration of Pluronic® F-98 increase the mean radius of the droplets generated decreases.

Example 5

Figure 8A:
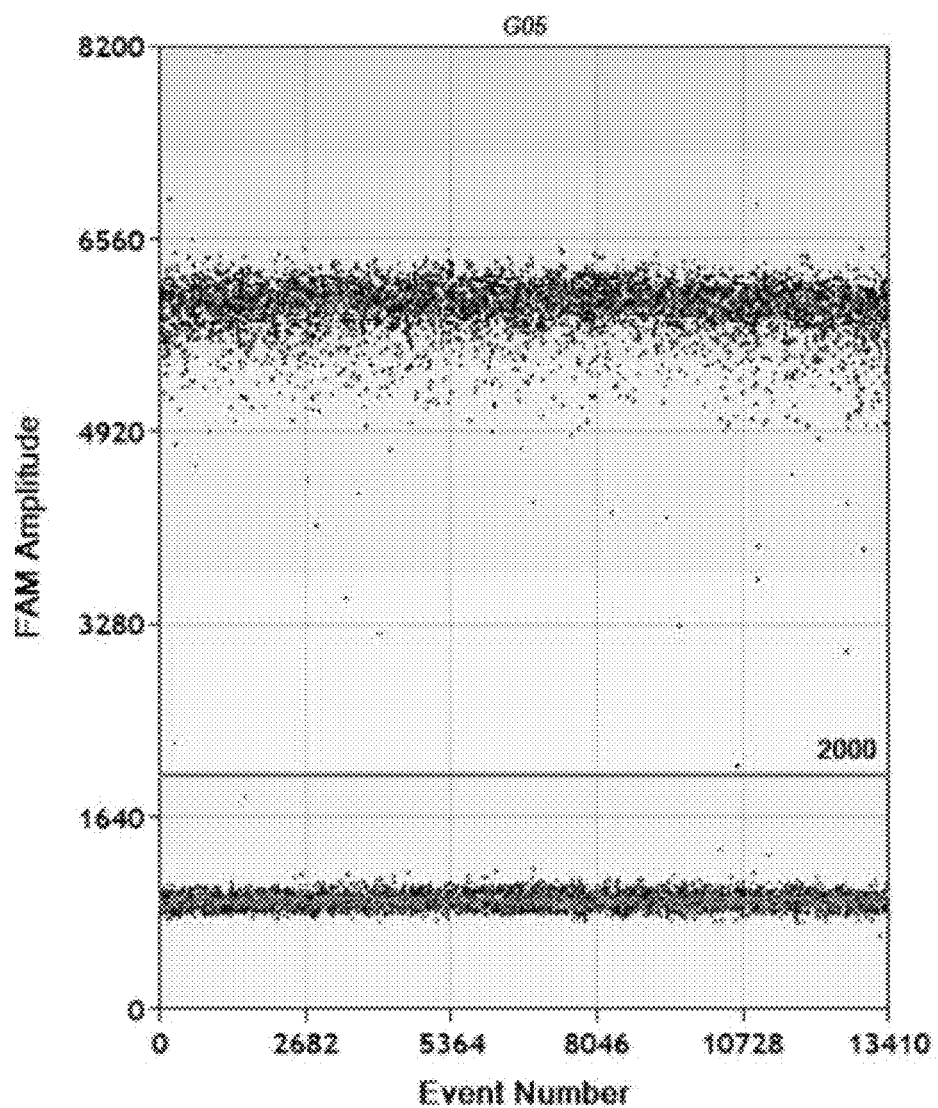
FIG. 8A illustrates a graphical representation of a single well in the optimized droplet digital polymerase chain reaction (ddPCR) system comprising of 2.5 mM fluorosurfactant XII in HEF-7500 as continuous phase and 0.50-0.75% w/w Pluronic® F-98, buffered, pH~8.3-8.4 as aqueous phase using the EvaGreen® intercalating dye.
Figure 8B:
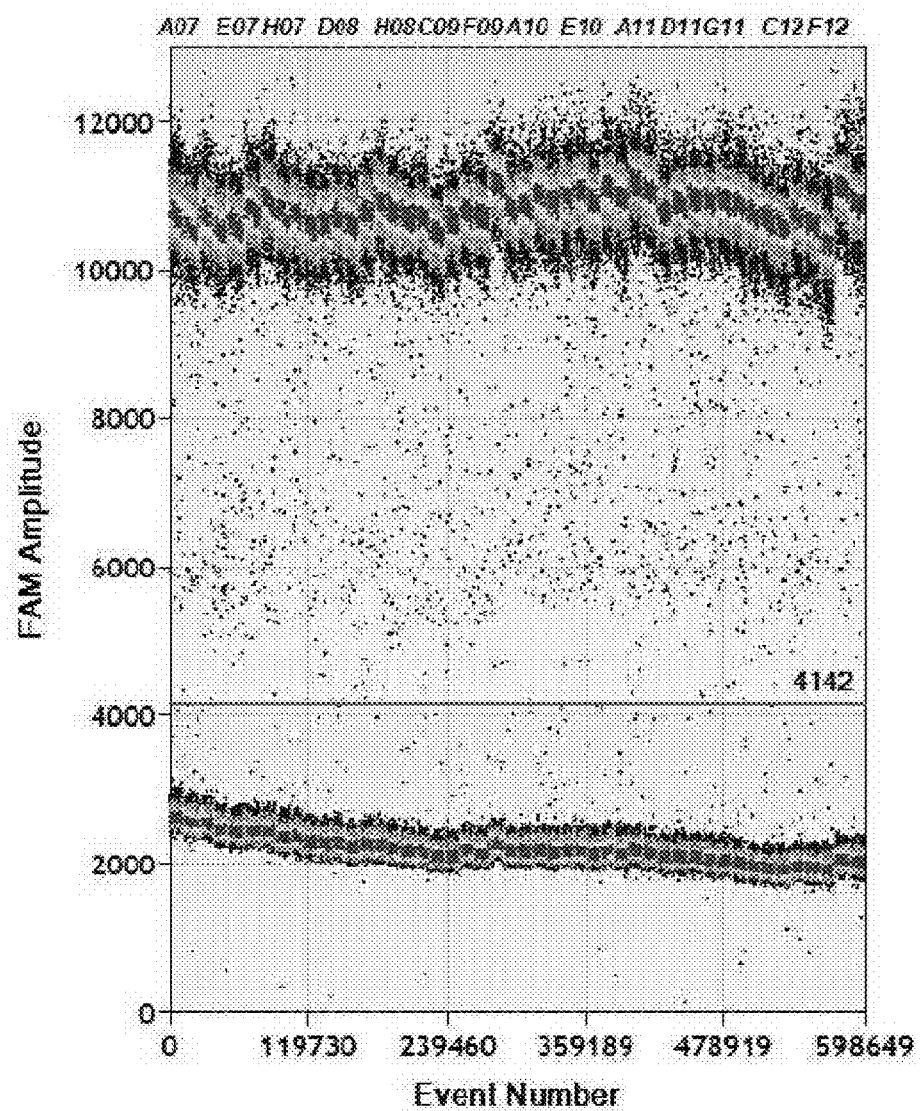
FIG. 8B illustrates a graphical representation for 96 wells in the optimized ddPCR system comprising 2.5 mM fluorosurfactant XII in HEF-7500 as a continuous phase and 0.50-0.75% w/w Pluronic® F-98, buffered, pH~8.3-8.4 as aqueous phase using the EvaGreen® intercalating dye, in accordance with an embodiment of the present disclosure.

FIGS. 8A and 8B shows the use of EvaGreen® dye and micro-emulsion (droplets) comprising of the combination of continuous phase (2.5 mM Bis-Krytox 157FS$_H$-PEG$_{1000}$, XII) and aqueous phase (050-0.75% w/w Pluronic®-F98, buffered, pH~8.3-8.4) in ddPCR assay.

This experiment involved performing a ddPCR assay using EvaGreen® dye under the optimized surfactant conditions (2.5 mM fluorosurfactant XII in HFE-7500, 0.50% w/w Pluronic® F-98 in buffered aqueous ddPCR master mix). Assay droplets (48 wells/reactions) containing 1 cpd. S. Aureus template, primers, DNA polymerase, 1× EvaGreen, and 0.50% w/w Pluronic® F-98, in a buffered aqueous ddPCR master mix were generated using the optimized droplet generation oil (2.5 mM fluorosurfactant XII in HFE-7500) by a standard method using a QX100™ Droplet Generator (Bio-Rad). Droplets were transferred to a 96-well PCR plate then cycled on a C1000 Touch™ Thermal Cycler (Bio-Rad) using a standard ddPCR thermal cycling protocol. Each well of droplets was then interrogated using a modified QX100™ Droplet Reader to count positive (high fluorescence intensity) and negative (low fluorescence intensity) droplets. FIG. 8A displays the ddPCR data for a single well/reaction, showing clear separation between the positive and negative droplets. FIG. 8B displays the ddPCR data for the 48 wells/reactions combined, again, illustrating distinct positive and negative bands. In this case it is also clear that the intercalating dye is not leaching, as the positive amplitude remains constant over the time taken for droplet interrogation (~1.5 hours).

Example 6

Scheme 4 shows an example of a synthetic route for the preparation of fluorosurfactant I.

Scheme 4

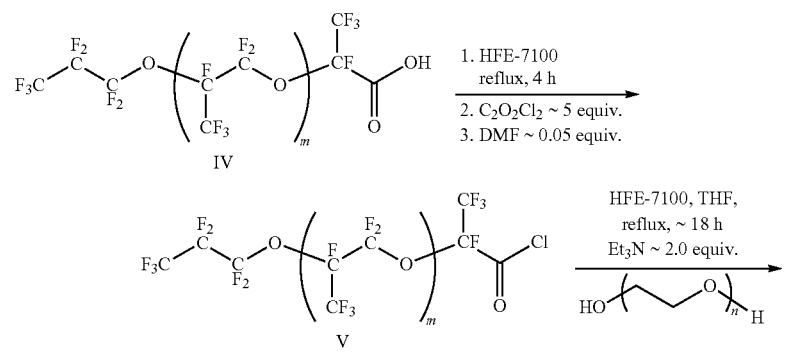

-continued

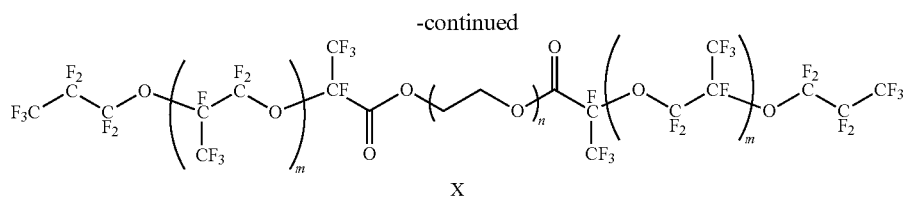

X

Solvent Preparation
Toluene

Toluene (125 ml) was dried over CaH$_2$ and solid Na flakes for at least 24 hours then freshly distilled prior to use. Benzophenone was added to the toluene during drying to act as an indicator, the toluene was a dark, vibrant, blue/purple color before distillation. Alternatively, toluene was dispensed directly from an anhydrous solvent dispenser if available.

HFE-7100

HFE-7100 (500 ml) was to be dried over CaH$_2$ for at least 24 hours then freshly distilled prior to use. Alternatively, HFE-7100 may be dispensed directly from an anhydrous solvent dispenser if available.

Tetrahydrofuran (THF)

THF (125 ml) was dried over CaH$_2$ and solid Na flakes for at least 24 hours then freshly distilled prior to use. Benzophenone was added to the THF during drying to act as an indicator, the THF must be a dark, vibrant, blue/purple color before distillation. Alternatively, THF may be dispensed directly from an anhydrous solvent dispenser if available.

Reagent Preparation

The MW of each new carboxylic acid XI lot number was determined by $^{19}$F NMR prior to use. PEG(1000) was dissolved in dry toluene (125 ml) then evaporated to dryness under reduced pressure (<10 mbar) at 60° C. to remove any traces of H$_2$O by azeotropic distillation (immediately before use). Oxalyl Chloride, Dimethylformamide and Triethylamine were used as supplied by Sigma-Aldrich. To ensure the anhydrous integrity of oxalyl chloride and triethylamine were both purchased fresh prior to use. The reagents were not used for manufacturing if they had been opened for more than a month prior to use.

Synthetic Method

Carboxylic acid XI (300.0 gram (g), 49.63 millimoles (mmol)) and dimethylformamide (0.192 milliliter (ml), 2.48 mmol) were added to a 1000 ml round bottom flask (RBF) equipped with a magnetic stirring bar. The RBF was purged with N$_2$ (or Ar), stoppered with a rubber septum, topped with a N$_2$ (or Ar) filled balloon, and then freshly distilled HFE-7100 (250 ml) was added by syringe. A reflux condenser topped with a rubber septum and N$_2$ (or Ar) filled balloon was attached to the RBF, then the contents were heated (sand bath set at 90° C.) with stirring (~650 revolutions per minute (rpm)) for 5 minutes before the slow addition of oxalyl chloride (21 ml, 245 mmol) by syringe. The clear solution turned a clear, light yellow color, and a large amount of gas was produced (CAUTION!), excess pressure was relieved with an uncapped needle (19 gauge), and manual venting of the rubber septum if required. Following stirring for 10 minutes at reflux, the solution frothed again, produced a large amount of gas, and became a milky white color. Following a further 5 minutes stirring at reflux the solution returned to an opaque, light yellow color. After an additional 15 minutes stirring at reflux, the solution had become a clear, light yellow color.

This solution was stirred at reflux (60° C.) for a total of 4 hours, during this time the solution became a clear orange color and contained a small amount of suspended solid brown particulate. The solution was allowed to cool to room temperature, and then excess solvent and oxalyl chloride were removed under reduced pressure (<10 mbar) at 60° C. to give the crude acid chloride as an orange oil containing suspended brown particulate.

Freshly distilled HFE-7100 (250 ml) was added to the crude acid chloride in the 1000 ml RBF (which was capped with a rubber septum and N$_2$ (or Ar) filled balloon) by syringe. This solution was then refluxed with stirring (~650 rpm) at 60° C. (sand bath set at 90° C.) under N$_2$ (or Ar) for 5 minutes, before addition of a solution of PEG (24.8 g, 24.8 mmol) and triethylamine (14 ml, 100 mmol) in dry THF (125 ml) by syringe (or double-tipped needle, or an appropriate transfer line).

Note: The reaction mixture immediately fumed and turned a milky white color due to a large amount of white precipitate (NEt$_3$.HCl) forming.

This reaction mixture was refluxed at 66° C. (sand bath set at 90° C.) under N$_2$ (or Ar) with stirring (~650 rpm) for approximately 18 hours, during this time the reaction mixture became a tan color and a small amount of brown/black precipitate adhered to the walls of the RBF. The reaction mixture was allowed to cool to RT, then excess solvent and triethylamine were removed under reduced pressure (<10 mbar) at 60° C. to give the crude Formula I as an orange/tan semi-solid. The crude product was dissolved in HFE-7100 (1750 ml), then added to a 2000 ml separating funnel, this solution was allowed to settle overnight (the solid impurities floated to the top of the HFE-7100). The fluorous phase was slowly filtered through a fritted Buchner funnel (porosity 4-8 μm) under vacuum in portions of ~500 ml and collected in a 1000 ml pear-shaped evaporating flask. The solvent was evaporated under reduced pressure at 60° C. following each collection. The remaining light tan solid residue present in the 2000 ml separating funnel was washed with additional HFE-7100 (250 ml). This solution was allowed to settle overnight. The solution was then slowly filtered through a fritted Buchner funnel (porosity 4-8 μm) under vacuum in portions of ~500 ml and collected in a 1000 ml pear-shaped evaporating flask. The solvent was evaporated under reduced pressure at 60° C. following each collection. The residue was combined with the previous fluorous extracts, then evaporated to dryness under reduced pressure (<10 mbar) at 70° C. to yield Formula I (323.9 g, 25.02 mmol) as an extremely viscous orange/brown syrup.

Example 7

Figure 9:
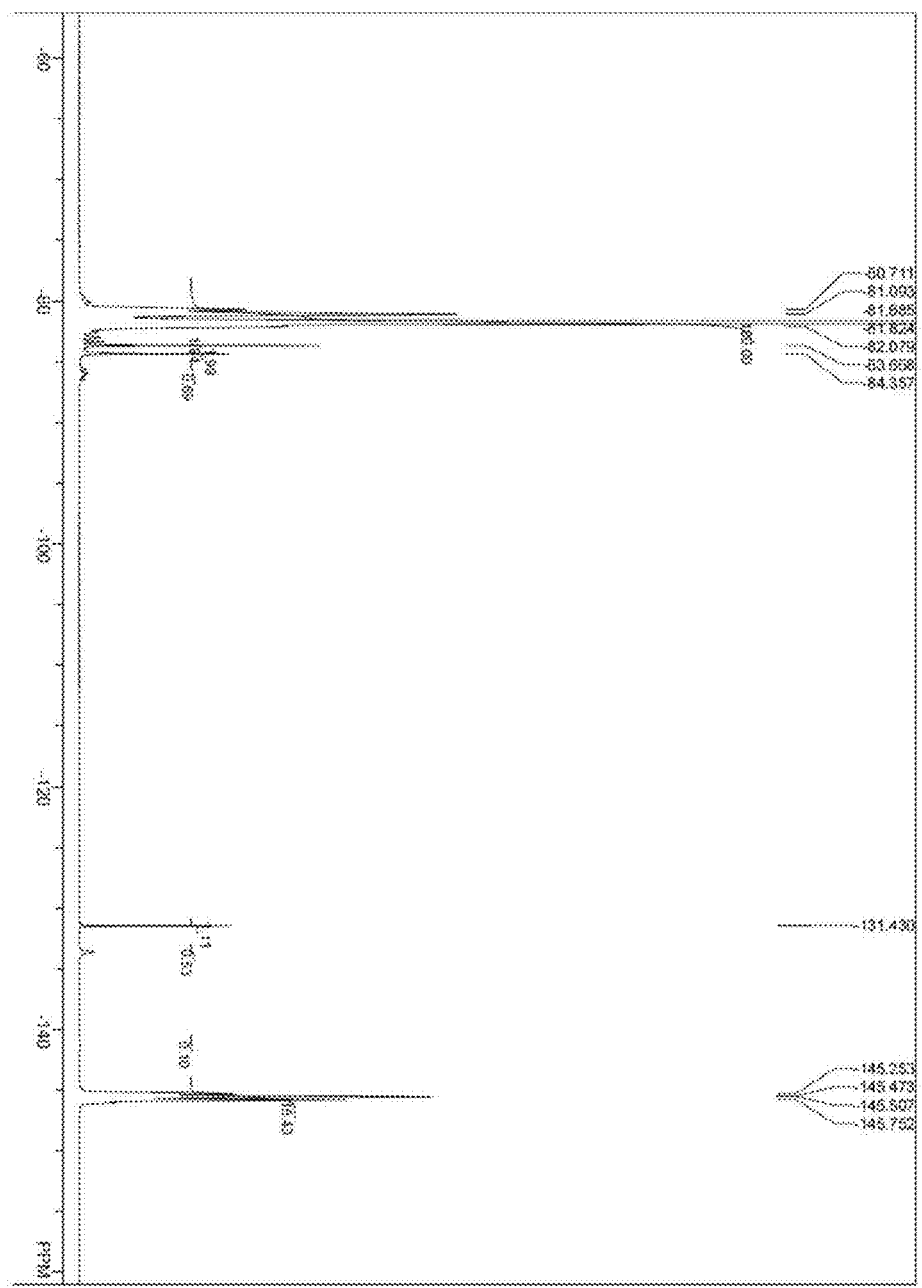
FIG. 9 shows the $^{19}$F NMR spectrum of compound XI.

Characterization of the Fluorosurfactant XII
NMR Spectroscopy of Carboxylic Acid XI A $^{19}$F NMR spectrum of the specific lot of starting carboxylic acid XI used for synthesis was collected 'neat' at 50° C. with a total of 128 scans. The typical $^{19}$F NMR spectrum for the carboxylic acid is shown in FIG. 9. The actual average molecular weight (MW) for carboxylic acid XI was calculated based on the $^{19}$F NMR spectra. The average MW calculated should be within 5500-6500 atomic mass units (amu).

Figure 12:
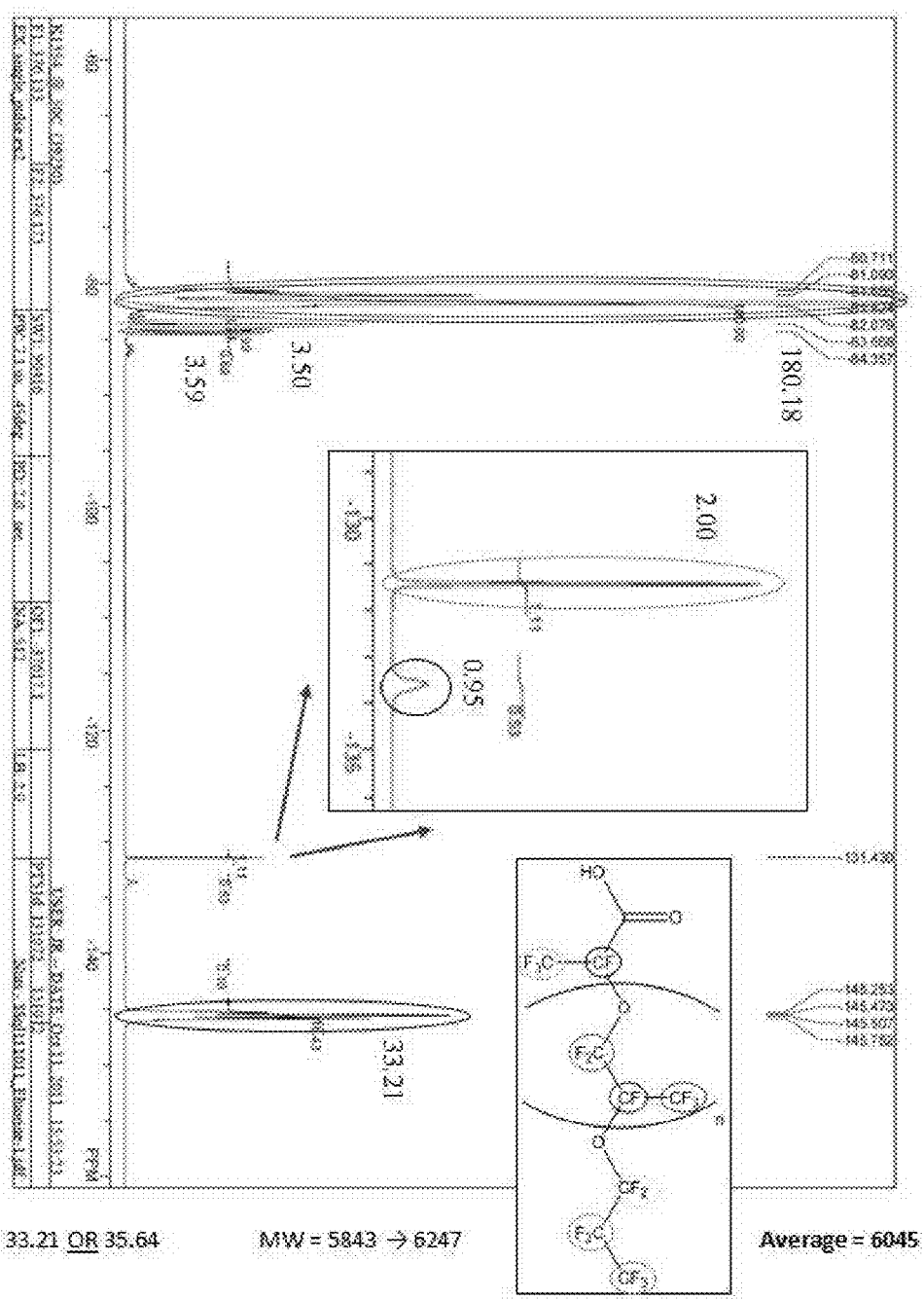
FIG. 12 shows the peaks of interest for the calculation of the average molecular weight of compound XI based on its $^{19}$F NMR spectrum.

An example of MW calculation from $^{19}$F NMR spectrum is shown in FIG. 12. The C$\underline{F}_2$—CF$_3$ signal was 'easily' identified and well resolved with reliable integration (~−131 ppm). To calculate the MW range, the integral of the C$\underline{F}_2$—CF$_3$ (~−131 ppm) signal was compared to the integral of the signals from the repeating monomer units (~−145 ppm and ~−81 ppm) to determine n.
The three integrals were normalized so that the C$\underline{F}_2$—CF$_3$ signal was equal to 2.00:

So: 1.11×1.80=2.00,18.43×1.80=33.21, and 100.00× 1.80=180.18

So: $n$=[Int(C$\underline{F}$—CF$_2$)/1]/[Int(C$\underline{F}_2$—CF$_3$)/2] e.g. $n$=(33.21/1)/(2.00/2)=33.21

OR $n$=[Int((C$\underline{F}_2$—CF+C$\underline{F}_3$—CF—CF$_2$)-2)/5]/[Int(C$\underline{F}_2$—CF$_3$)/2] e.g. $n$=((180.18-2)/5)/(2.00/2)=35.64

Once 'n' is determined, MW's of repeating monomer and terminal units were added together:

MW$_{(carboxylic\ acid\ XI)}$=MW(C$_2$F$_4$COOH)+[$n$×MW(C$_3$F$_6$O)]+MW(C$_3$F$_7$O)

=145.03+[$n$×(166.02)]+185.02

So: MW$_{(carboxylic\ acid\ XI)}$=145.03+(33.21×166.02)+ 185.02=5843.57

OR =145.03+(35.64×166.02)+185.02=6247.00

So: Average MW$_{(carboxylic\ acid\ XI)}$=(5843.57+ 6247.00)/2=6045.29

NMR Spectroscopy of Fluorosurfactant XII

The sample of fluorosurfactant XII for $^{19}$F and $^{13}$C NMR analysis was prepared by dissolving 1 g of the product in 0.2 ml of hexafluorobenzene (C$_6$F$_6$). Approximately 0.7 ml of this solution was transferred to a standard NMR tube (5 mm×180 mm) to fill the tube to a depth of approximately 5 cm. The $^{19}$F spectrum was collected 'neat' at 50° C. with a total of 128 scans, the $^{13}$C spectrum is collected 'neat' at 50° C. scanning continuously for about 2 hours.

Figure 10:
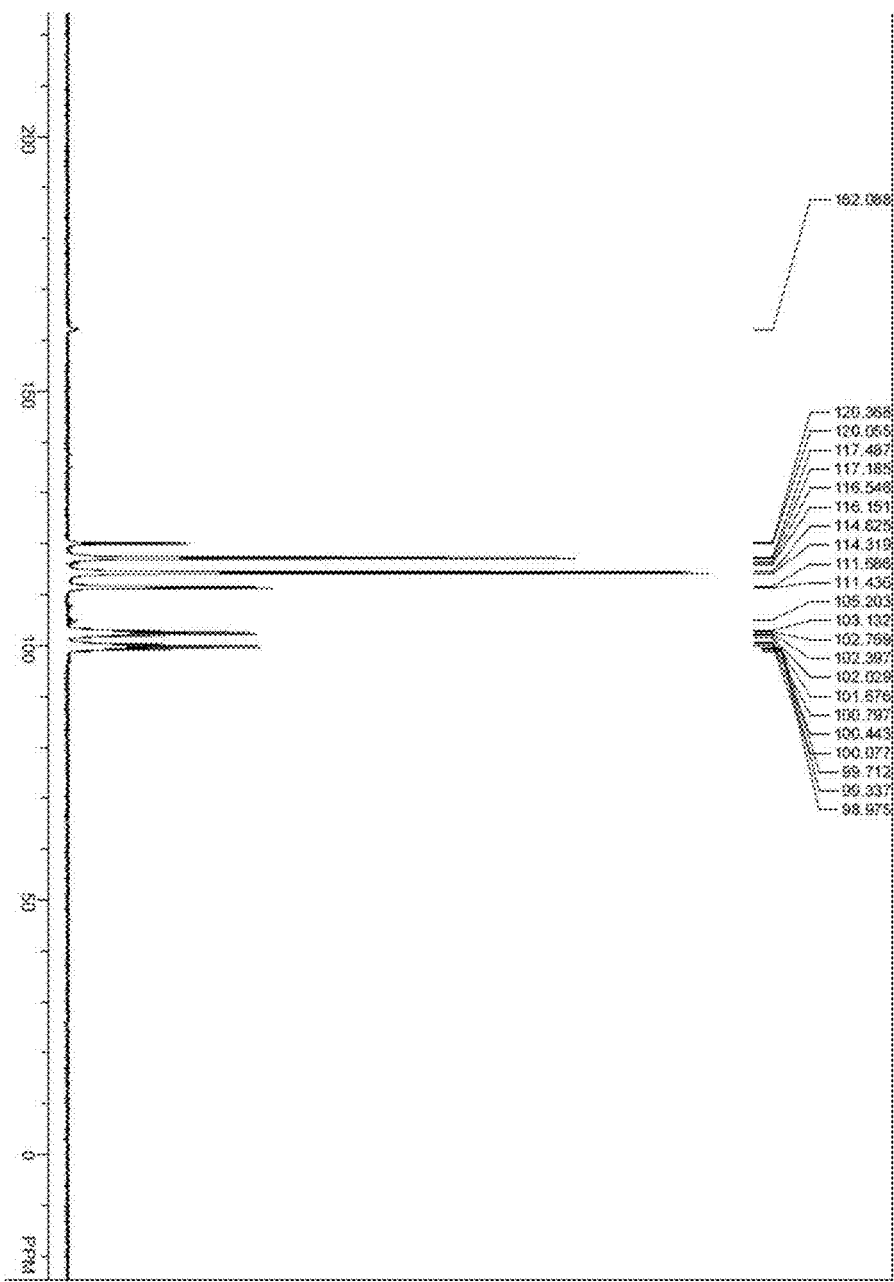
FIG. 10 shows the $^{13}$C NMR spectrum of compound XI.
Figure 11:
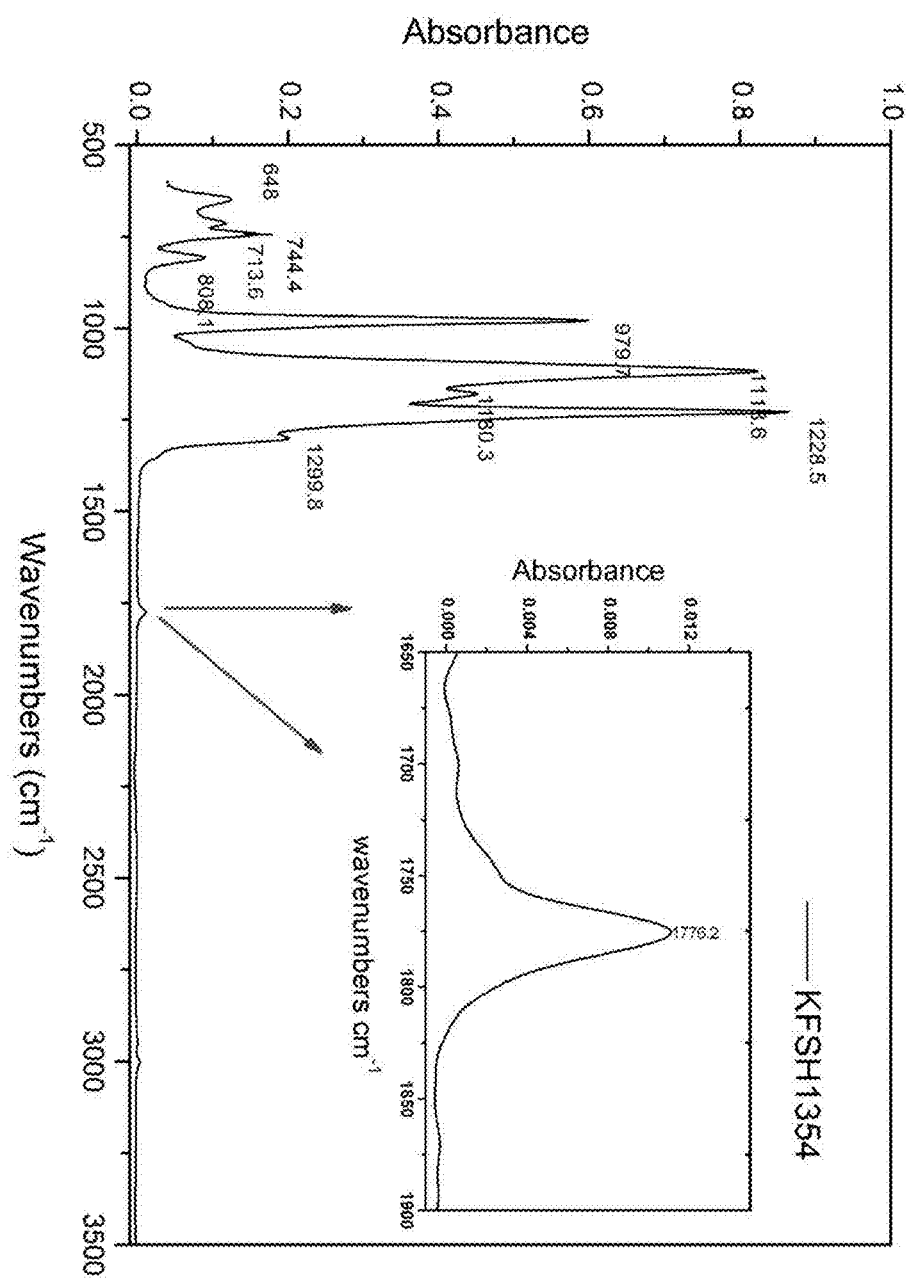
FIG. 11 shows the FTIR spectrum of compound XI.
Figure 13:
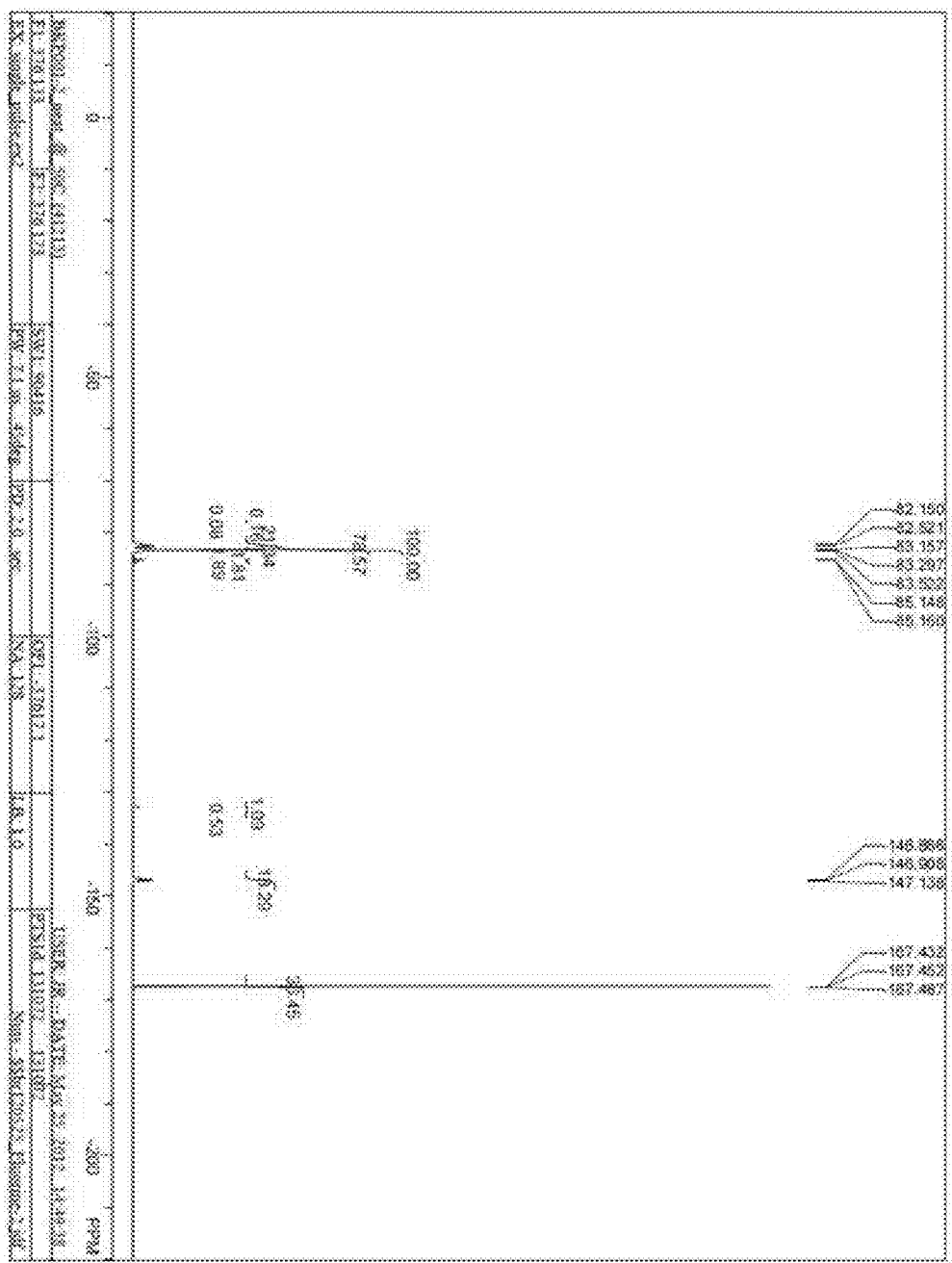
FIG. 13 shows the $^{19}$F NMR spectrum of compound XII.
Figure 14:
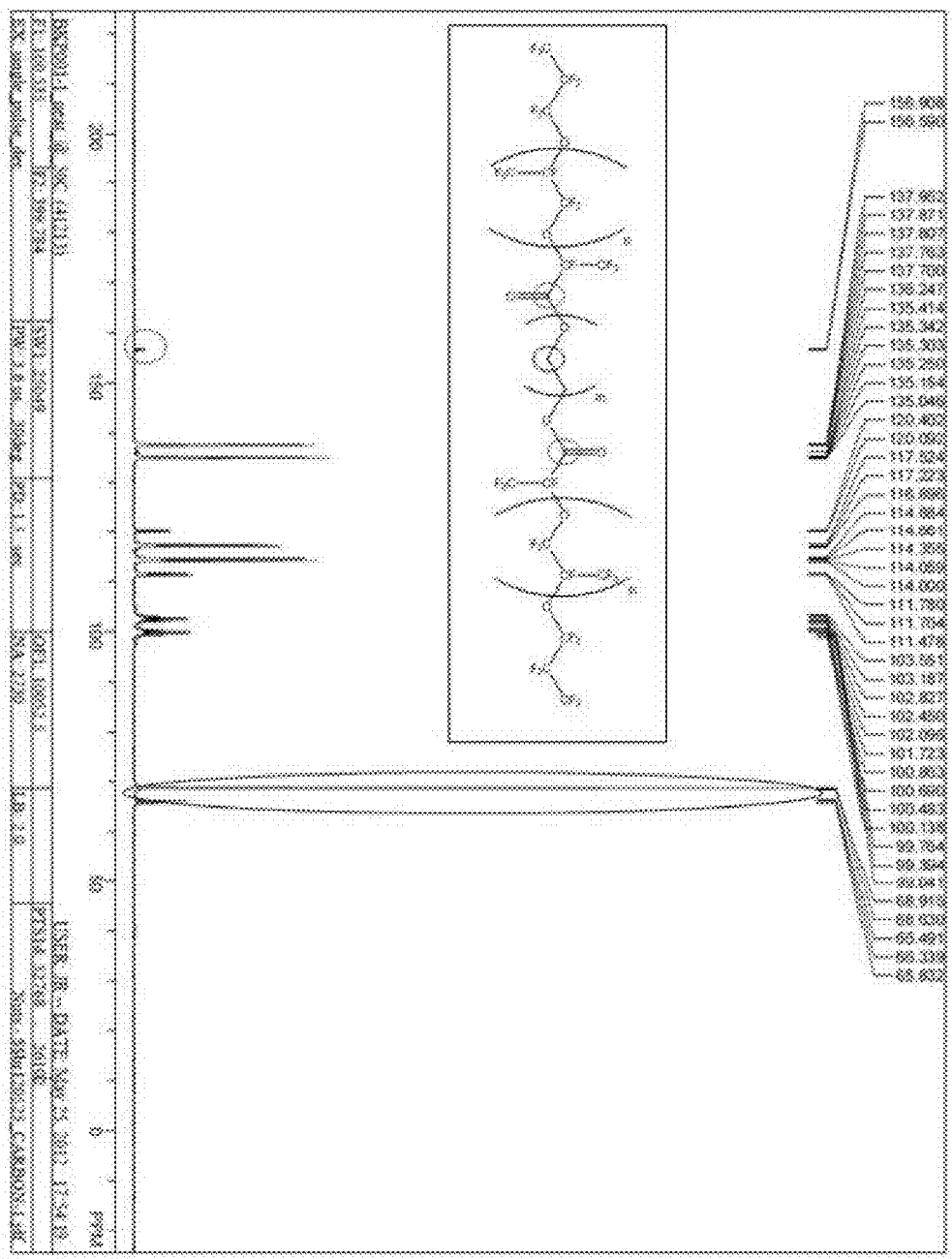
FIG. 14 shows the $^{13}$C NMR spectrum of compound XII.
Figure 15:
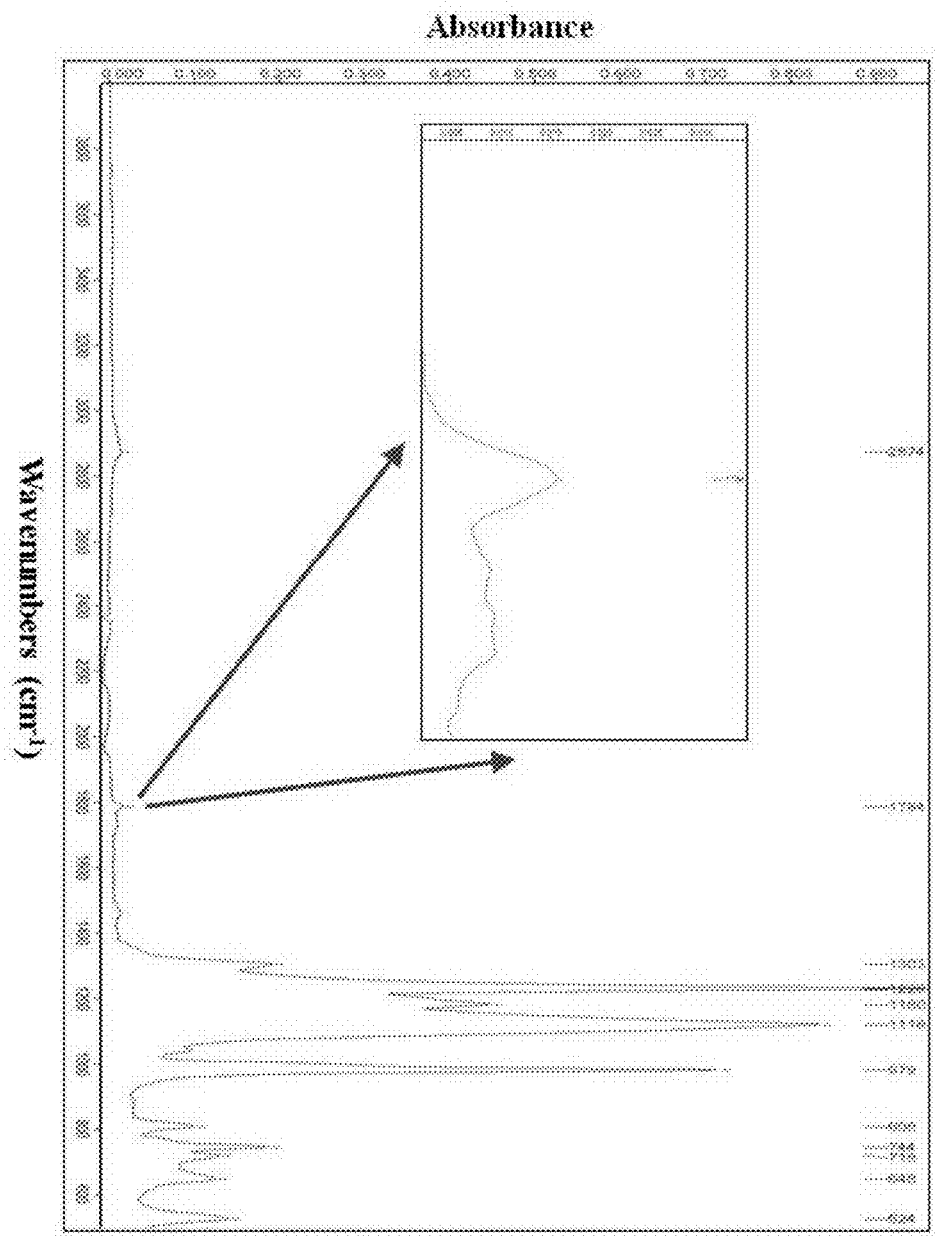
FIG. 15 shows the FTIR spectrum of compound XII.

Typical $^{19}$F and $^{13}$C spectra of fluorosurfactant XII are shown in FIGS. 13 and 14 respectively. Of particular interest in the $^{13}$C NMR spectra of fluorosurfactant XII is the resonance due to the carbonyl carbon (C=O) at about 157 ppm. This resonance has undergone a significant up-field shift when compared to the resonance of the corresponding carbonyl carbon at about 162 ppm in the $^{13}$C NMR spectra of the carboxylic acid starting material XI (FIG. 10).

In the $^{13}$C NMR spectrum of high purity fluorosurfactant XII, a relatively weak resonance due to the carbonyl carbons (C=O) of the two ester linkages was present at 157±2 ppm, while the resonance due to the carbonyl carbon (C$\underline{O}$OH) of the carboxylic acid XI observed at 162±2 ppm was absent.

ATR-FTIR

This qualitative technique was used to confirm the conversion of the carbonyl carbon of the carboxylic acid XI starting material to the two ester linkages formed in the fluorosurfactant XII. This analysis was performed using the Bruker Tensor 27 IR spectrophotometer with the Platinum ATR module installed. Following collection of the background spectrum, a small drop of the fluorosurfactant XII sample was smeared across the ATR crystal and the spectrum of the sample was collected with the following parameters; resolution=4, number of scans=32, and wavelength range=4000 to 500 cm$^{-1}$.

A peak correlating to the C=O stretch was found to be present with the maximum occurring at about 1784±6 cm$^{-1}$ indicating the conversion of the carboxylic acid XI to the desired fluorosurfactant XII.

Fluorescence

A custom quantitative technique was developed in house to determine the remaining amount of carboxylic acid XI starting material left in the fluorosurfactant XII product as an impurity, and to determine the percentage purity of the fluorosurfactant XII.

A 100 ml of a 1.000 mM stock solution of the carboxylic acid XI was prepared in a 100 ml volumetric flask. Nine subsequent standards were prepared from stock solutions according to the volumes indicated in the Table 1 below (final concentration range of 1.000 mM to 0.010 mM). 25 ml of a 10× solution of SYBR green in deionized H$_2$O was also prepared in a 25 ml volumetric flask.

The amount of carboxylic acid XI required for 1.000 mM stock was determined by the following formula Mass (carboxylic acid XI) in grams=0.001 M×0.1 L×Actual MW of carboxylic acid XI as determined by $^{19}$F NMR analysis Table 1. The Prepared Stock Solutions of Carboxylic Acid XI.

| Desired stock concentration (mM) | Required concentration of stock (mM) | Required volume of stock (ml) | Required volume of HFE-7500 (ml) | Final volume (ml) |
|---|---|---|---|---|
| 1.000 (stock) | — | — | 100.0 | 100.0 |
| 0.750 | 1.000 | 7.5 | 2.5 | 10.0 |
| 0.500 | 1.000 | 5.0 | 5.0 | 10.0 |
| 0.400 | 1.000 | 4.0 | 6.0 | 10.0 |
| 0.300 | 1.000 | 3.0 | 7.0 | 10.0 |
| 0.200 | 1.000 | 2.0 | 8.0 | 10.0 |
| 0.100 | 1.000 | 5.0 | 45.0 | 50.0 |
| 0.075 | 0.100 | 7.5 | 2.5 | 10.0 |
| 0.050 | 0.100 | 5.0 | 5.0 | 10.0 |
| 0.010 | 0.100 | 1.0 | 9.0 | 10.0 |

A Varian Cary Eclipse spectrofluorimeter instrument was used for the present analysis and the temperature was set to 20° C. 2 ml of the carboxylic acid XI 0.010 M stock solution was transferred to clean 3 mL quartz cuvette, on which was carefully overlaid 1 ml of the SYBR 10× stock solution. The fluorescence spectra of the fluorous phase of this sample was then collected at ~542 nm over a period of time (~1 hour) at 20° C. using a Varian Cary Eclipse spectrofluorimeter (Agilent Technologies, Inc.).

The above steps were repeated for the additional nine standards prepared and for the 2.5 mM solution fluorosurfactant XII containing an unknown amount of acid XI as purity. Between each run, the quartz cuvette was thoroughly rinsed with 70% EtOH solution and HFE-7500 and was dried using compressed air.

Figure 16A:
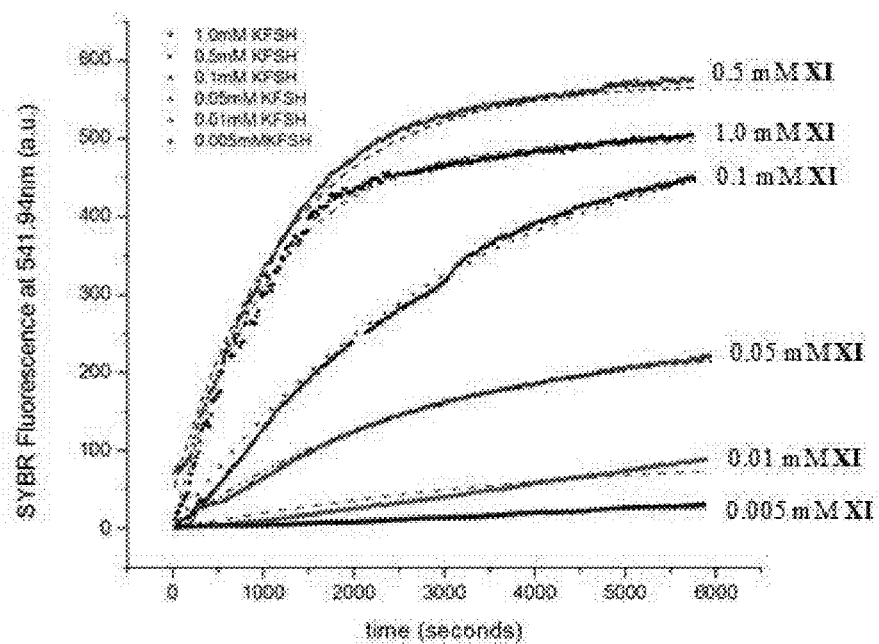
FIG. 16A shows the pseudo-first order kinetic leaching profiles for the compound XI standards.
Figure 16B:
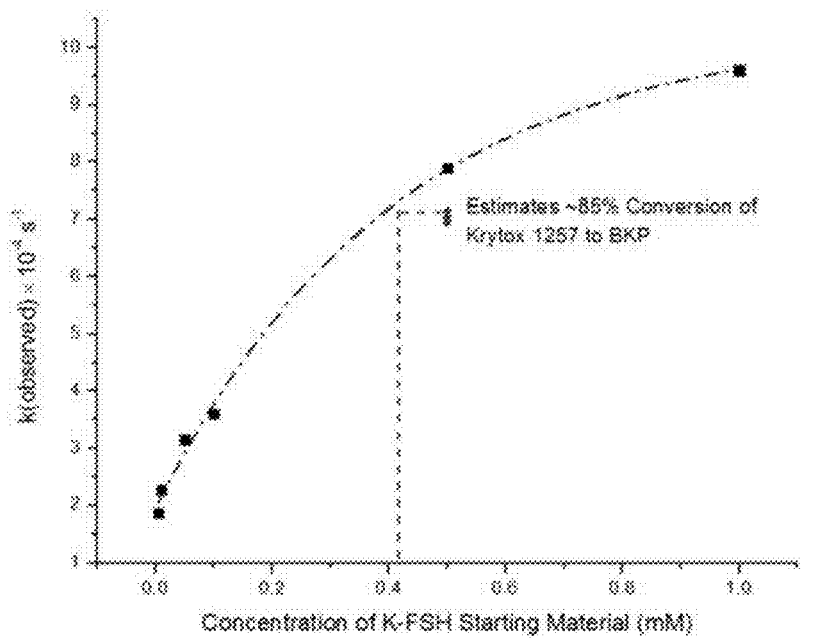
FIG. 16B shows the calibration curve used for calculating the purity of compound XII.

The kinetic leaching profiles of each of the above solutions were fitted to the equation 1 shown below to determine the pseudo-first order kinetic rate constant (k) for each of the standards and the unknown fluorosurfactant XII sample (FIG. 16A). A Plot of k versus concentration for the standards was obtained to construct a calibration curve shown in FIG. 16B.

$$[B] = [B]_{\circ} \cdot e^{-k[A] \cdot t} \qquad \text{Equation 1}$$

where:

| [B] = fluorescence intensity | [B]$_{\circ}$ = fluorescence intensity at t = 0 |
|---|---|
| e = natural log | k = rate constant |
| [A]$_{\circ}$ = 1 | t = time |

The unknown concentration of carboxylic acid XI in the 2.5 mM fluorosurfactant XII sample was determined from the calibration curve. For example in FIG. 16B, the pseudo first kinetic rate constant of 7.25×10-4 sec-1 corresponds to about 0.42 mM concentration of the carboxylic acid XI. The purity of the synthesized fluorosurfactant was determined using the formulas below:

Theoretical mass of fluorosurfactant in 1 L of 2.5 mM *XII*

= concentration (M) × volume (L) × MW (*XII*)

= 0.0025 (M) × 1 (L) × 13054

= 32.64 g

Actual mass of carolxylic acid *XI* in 1 L of 2.5 mM *XII*:

= concentration (M) (from the calibration curve) × volume (L) × MW (*XI*)

= (0.42 (mM)/1000) × 1 (L) × 6045 = 2.54 g

Actual mass of fluorosurfactant in 1 L of 2.5 mM *XII*

= Theoretical mass fluorosurfactant *XII* (g) −

Calculated mass of carboxylic acid *XI* (g)

= 32.64 (g) − 2.54 (g)

= 30.10 (g)

Purity of fluorosurfactant *XII* (% w/w)

= $\frac{\text{Actual mass fluorosurfactant } XII \text{ (g)}}{\text{Theoretical mass fluorosurfactant } XII \text{ (g)}} \times \frac{100}{1}$ = (30.10 (g)/32.64 (g)) × (100/1)

= 92.2% w/w

Elemental Analysis

Analysis was carried out for the elements C, H and F and each analysis was performed in duplicate. The theoretical molecular formula and percentage composition of the elements C, H and F were calculated based upon the average molecular weights of the starting materials. The elemental results were recorded and compared with the theoretical elemental composition. The difference between the theoretical elemental composition and actual elemental analysis results was less than 0.5%. A representative data from the elemental analysis of fluorosurfactant XII, average molecular formula=$C_{260}H_{90}O_{95}F_{430}$, is tabulated in Table 2.

TABLE 2

Elemental analysis of fluorosurfactant XII.

| Element (theoretical) | Fluorosurfactant X11 | | | |
|---|---|---|---|---|
| | Analysis 1 | Δ | Analysis 2 | Δ |
| C—24.20% | 24.12% | 0.08% | 24.13% | 0.07% |
| H—0.70% | 0.58% | 0.12% | 0.52% | 0.18% |
| O—11.78% | — | — | — | — |
| F—63.31% | 63.47% | 0.16% | 63.62% | 0.31% |

Note:
O content is unable to be determined if F content exceeds 30%

Example 8. Analysis of Fluorosurfactant Mixtures

Figure 17:
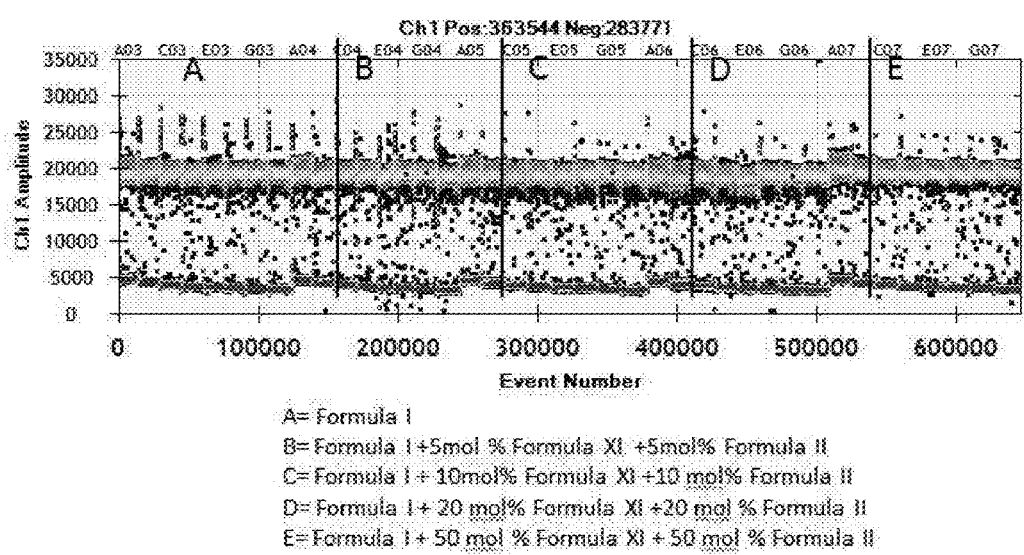
FIG. 17 illustrates a graphical representation for 96 wells in the optimized ddPCR system comprising various fluorosurfactant mixtures using the EvaGreen® intercalating dye, in accordance with an embodiment of the present disclosure.

FIG. 17 shows the analysis of EvaGreen® dye and micro-emulsion (droplets) comprising the various fluorosurfactant mixtures in a ddPCR assay.

This experiment involved performing a ddPCR assay using EvaGreen® dye under the various surfactant conditions, wherein: A=Formula I; B=Formula I+5 mol % Formula XI+5 mol % Formula II; C=Formula I+10 mol % Formula XI+10 mol % Formula II; D=Formula I+20 mol % Formula XI+20 mol % Formula II; E=Formula I+50 mol % Formula XI+50 mol % Formula II. Assay droplets (96 nwells/reactions) containing 1 cpd. *S. Aureus* template, primers, DNA polymerase, 1× EvaGreen, and 0.50% w/w Pluronic® F-98, in a buffered aqueous ddPCR master mix were generated using the optimized droplet generation oil (2.5 mM fluorosurfactant XII in HFE-7500) by a standard method using a QX200™ Droplet Generator (Bio-Rad). Droplets were transferred to a 96-well PCR plate then cycled on a C1000 Touch™ Thermal Cycler (Bio-Rad) using a standard ddPCR thermal cycling protocol. Each well of droplets was then interrogated using a QX200™ Droplet Reader to count positive (high fluorescence intensity) and negative (low fluorescence intensity) droplets. FIG. 17 displays the ddPCR data for the 96 wells/reactions combined, illustrating distinct positive and negative bands. The spikes seen in window A indicate large extra-cluster droplets, which are reduced upon addition of various amounts of formula II and formula XI.

While exemplary examples and embodiments of the present invention have been shown and described herein, it will be obvious to those skilled in the art that such examples and embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting a target nucleic acid, the method comprising:
   (a) providing an oil composition comprising an oil and a fluorosurfactant mixture, wherein said fluorosurfactant mixture includes
      a triblock copolymer comprising polyethylene glycol (PEG) polymer covalently linked by an ester bond to polyhexafluoropropylene oxide (PFPE) at both ends,
      a diblock copolymer comprising a PEG block covalently linked by an ester bond to a PFPE block at only one end, and
      a PFPE carboxylic acid;
   (b) providing an aqueous composition comprising a target nucleic acid, a non-ionic non-fluorosurfactant and an intercalating dye;
   (c) contacting the oil composition of a) with the aqueous composition of b), thereby generating a plurality of droplets suspended in a continuous phase;
   (d) thermally cycling said plurality of droplets to amplify said target nucleic acid; and
   (e) detecting said target nucleic acid, wherein said detecting comprises measuring fluorescence from said intercalating dye.

2. The method of claim 1, wherein said triblock copolymer is of the formula:

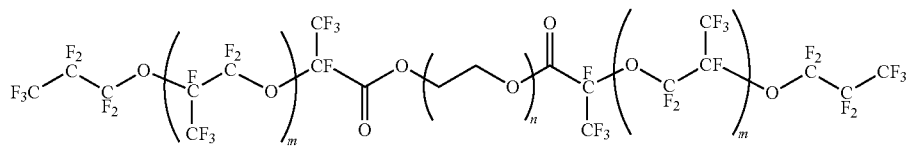

wherein m is a number from about 10 to 100; n is a number from about 10 to 60.

3. The method of claim 1, wherein said triblock copolymer constitutes at least about 90% (w/w) of the fluorosurfactant mixture.

4. The method of claim 2, wherein m is from about 20 to 40, and n is from about 15 to 30.

5. The method of claim 4, wherein m is about 35 and n is about 22.

6. The method of claim 1, wherein said triblock copolymer has a hydrophilic-lipophilic balance of at least about 0.5.

7. The method of claim 1, wherein said triblock copolymer has a hydrophilic-lipophilic balance of less than about 5.0.

8. The method of claim 1, wherein said triblock copolymer has a hydrophilic-lipophilic balance in a range from about 0.5 to 5.0.

9. The method of claim 1, wherein said triblock copolymer has a hydrophilic-lipophilic balance of about 1.5.

10. The method of claim 1, wherein said non-ionic non-fluorosurfactant is a copolymer of ethylene oxide and propylene oxide.

11. The method of claim 10, wherein said non-ionic non-fluorosurfactant is a triblock copolymer of polyethylene oxide-polypropylene oxide-polyethylene oxide.

12. The method of claim 1, wherein said non-ionic non-fluorosurfactant is Pluronic®.

13. The method of claim 1, wherein said non-ionic non-fluorosurfactant is Pluronic® F-98.

14. The method of claim 13, wherein the concentration of said Pluronic® F-98 is in a range from about 0.1%-3.0% (weight percent).

15. The method of claim 1, wherein said oil comprises a fluorous oil.

16. The method of claim 15, wherein said fluorous oil is 2-trifluoromethyl-3-ethoxydodeca-fluorohexane (HFE-7500) or 1,1,1,2,2,3,4,5,5,5-decafluoro-3-methoxy-4-(trifluoromethyl)pentane (HFE-7300).

17. The method of claim 1, wherein said continuous phase comprises said oil.

18. The method of claim 1, wherein said plurality of droplets is aqueous droplets encapsulated by said oil.

19. The method of claim 18, wherein less than about 5% of said intercalating dye is detected outside of the aqueous phase of said aqueous droplets after about 50 thermal cycles.

20. The method of claim 18, wherein less than about 10% of said intercalating dye is detected outside of the aqueous phase of said aqueous droplets after about 100 thermal cycles.

21. The method of claim 1, wherein on average each of said plurality of droplets comprises less than $5.5 \times 10^{12}$ target nucleic acids after thermal cycling.

22. The method of claim 1, wherein said intercalating dye includes EvaGreen® dye.

* * * * *